(12) United States Patent
Jung et al.

(10) Patent No.: US 9,017,827 B2
(45) Date of Patent: *Apr. 28, 2015

(54) INDENOCARBAZOLE COMPOUND FOR OPTOELECTRONIC DEVICE, ORGANIC LIGHT EMITTING DIODE INCLUDING THE SAME AND DISPLAY INCLUDING THE ORGANIC LIGHT EMITTING DIODE

(75) Inventors: Sung-Hyun Jung, Uiwang-si (KR); Hyung-Sun Kim, Uiwang-si (KR); Ho-Jae Lee, Uiwang-si (KR); Eun-Sun Yu, Uiwang-si (KR); Mi-Young Chae, Uiwang-si (KR); Young-Hoon Kim, Uiwang-si (KR); Ja-Hyun Kim, legal representative, Boryeong (KR)

(73) Assignee: Cheil Industries, Inc., Gumi-si, Kyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,019

(22) Filed: Dec. 23, 2011

(65) Prior Publication Data

US 2012/0091446 A1     Apr. 19, 2012

Related U.S. Application Data

(63) Continuation of application No. PCT/KR2010/004156, filed on Jun. 25, 2010.

(30) Foreign Application Priority Data

Jun. 25, 2009 (KR) .......................... 10-2009-0057234

(51) Int. Cl.
| | |
|---|---|
| *H01L 51/54* | (2006.01) |
| *C07D 401/14* | (2006.01) |
| *C07D 403/14* | (2006.01) |
| *C07D 403/04* | (2006.01) |
| *C07D 401/04* | (2006.01) |
| *H01L 51/00* | (2006.01) |
| *C09K 11/06* | (2006.01) |
| *H05B 33/14* | (2006.01) |
| *C09B 57/00* | (2006.01) |

(Continued)

(52) U.S. Cl.
CPC ............ *H01L 51/0072* (2013.01); *C09K 11/06* (2013.01); *C09K 2211/1011* (2013.01); *C09K 2211/1018* (2013.01); *C09K 2211/1029* (2013.01); *C09K 2211/1074* (2013.01); *H05B 33/14* (2013.01); *C09B 57/00* (2013.01); *C09B 57/008* (2013.01); *H01L 51/0067* (2013.01); *H01L 51/42* (2013.01); *H01L 51/50* (2013.01); *C07D 401/14* (2013.01); *C07D 401/04* (2013.01); *C07D 403/04* (2013.01); *C07D 403/14* (2013.01); *Y10S 428/917* (2013.01)

(58) Field of Classification Search
None
See application file for complete search history.

(56) References Cited

U.S. PATENT DOCUMENTS 5,759,444 A * 6/1998 Enokida et al. .......... 252/301.16
5,942,340 A    8/1999 Hu et al.

(Continued)

FOREIGN PATENT DOCUMENTS

DE    102006031990 A1      1/2008
DE    102008017591 A1 *   10/2009

(Continued)

OTHER PUBLICATIONS

Son et al. "Analyzing Bipolar Carrier Transport Characteristics of Diarylamino-Substituted Heterocyclic Compounds in Organic Light-Emitting Diodes by Probing Electroluinescence Spectra" Chem. Mater. 2008, 20, 4438-446. Date of online publication: Jun. 14, 2008.*

(Continued)

*Primary Examiner* — Andrew K Bohaty
(74) *Attorney, Agent, or Firm* — Lee & Morse, P.C.

(57) ABSTRACT

A compound for an organic optoelectronic device, an organic light emitting diode, and a display device, the compound including sequentially combined substituents represented by the following Chemical Formulae 1 to 3:

[Chemical Formula 1]

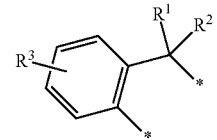

[Chemical Formula 2]

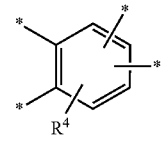

[Chemical Formula 3]

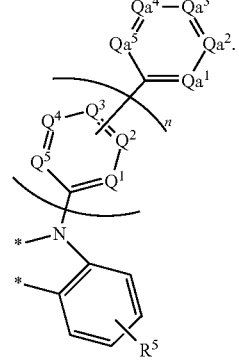

5 Claims, 9 Drawing Sheets

(51) Int. Cl.
*H01L 51/42* (2006.01)
*H01L 51/50* (2006.01)

(56) References Cited

U.S. PATENT DOCUMENTS

| | | |
|---|---|---|
| 5,952,115 A | 9/1999 | Hu et al. |
| 2004/0189190 A1* | 9/2004 | Suzuri et al. ............... 313/504 |
| 2006/0063033 A1 | 3/2006 | Sohn et al. |
| 2006/0147753 A1 | 7/2006 | Sohn et al. |
| 2007/0085051 A1 | 4/2007 | Sohn et al. |
| 2008/0124455 A1 | 5/2008 | Shin et al. |
| 2009/0261717 A1 | 10/2009 | Buesing et al. |
| 2010/0187977 A1* | 7/2010 | Kai et al. .................. 313/504 |
| 2011/0037027 A1* | 2/2011 | Stoessel et al. .......... 252/301.16 |
| 2012/0068170 A1 | 3/2012 | Pflumm et al. |

FOREIGN PATENT DOCUMENTS

| | | |
|---|---|---|
| EP | 1777227 A1 | 4/2007 |
| JP | 2006-083386 A | 3/2006 |
| JP | 2011-521894 A | 7/2011 |
| JP | 2012-515734 A | 7/2012 |
| JP | 2012-528088 A | 11/2012 |
| KR | 10 2006-0025933 A | 3/2006 |
| KR | 10 2006-0080726 A | 7/2006 |
| KR | 10 2008-0047209 A | 5/2008 |
| KR | 10 2010-0003624 A | 1/2010 |
| KR | 10 2010-0129101 A | 12/2010 |
| WO | WO 2008056746 A1 * | 5/2008 |
| WO | WO-2009-124627 A1 | 10/2009 |
| WO | WO-2010-083873 A1 | 7/2010 |
| WO | WO-2010-136109 A1 | 12/2010 |

OTHER PUBLICATIONS

Tang, et al.; Organic electroluminescent diodes; Applied Physics Letters; Sep. 21, 1987; pp. 913-915; vol. 51, No. 12; American Institute of Physics; USA.
O'Brien, et al.; Improved energy transfer in electrophosphorescent devices; Jan. 18, 1999; pp. 442-444; vol. 74, No. 3; American Institute of Physics; USA.
Baldo, et al.; Very high-efficiency green organic light-emitting devices based on electrophosphorescence; Jul. 5, 1999; pp. 4-6; vol. 75, No. 1; American Institute of Physics; USA.
International Search Report in PCT/KR2010/004156, dated Feb. 11, 2011 (Name, et al.).
European Search Report in EP 10792365.8-1218/2447334, dated Dec. 4, 2012 (Jung, et al.).

* cited by examiner

INDENOCARBAZOLE COMPOUND FOR OPTOELECTRONIC DEVICE, ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATION

This application is a continuation of International Application No. PCT/KR2010/004156, entitled "Compound for Organic Photoelectric Device and Organic Photoelectric Device Including the Same," which was filed on Jun. 25, 2010, the entire contents of which are hereby incorporated by reference.

BACKGROUND

1. Field

Embodiments relate to a compound for an optoelectronic device, an organic light emitting diode including the same, and a display including the organic light emitting diode.

2. Description of the Related Art

An organic optoelectronic device is, in a broad sense, a device for transforming photo-energy to electrical energy or, conversely, a device for transforming electrical energy to photo-energy. As examples, organic optoelectronic devices may include an organic light emitting diode (OLED), a solar cell, a transistor, and the like. An organic light emitting diode has recently drawn attention due to the increase in demand for flat panel displays.

When current is applied to an organic light emitting diode, holes are injected from an anode and electrons are injected from a cathode. Then, injected holes and electrons move to a respective hole transport layer (HTL) and electron transport layer (ETL) and recombine to form a light emitting exciton in an emission layer. The light emitting excitons generate light while shifting to a ground state. The light emission material may be classified as a fluorescent material (using singlet excitons) and a phosphorescent material (using triplet excitons) according to light emitting mechanism. The fluorescent and phosphorescent materials may be used for a light emitting source of an organic light emitting diode.

When electrons are transported from the ground state to the exited state, a singlet exciton may undergo non-light emitting transition to a triplet exciton through intersystem crossing, and the triplet exciton may be transited to the ground state to emit light. Such light emission is referred to as phosphorescent emission. When the triplet exciton is transited, it may not directly transit to the ground state. Therefore, it may be transited to the ground state after the electron spin is flipped. Accordingly, a half-life (light emitting time, lifetime) of phosphorescent emission is longer than that of fluorescent emission.

When holes and electrons are recombined to produce a light emitting exciton, three times as many triplet light emitting excitons may be produced, compared to the amount of the singlet light emitting excitons. A fluorescent material has 25% of the singlet-exited state and a limit in luminous efficiency. On the other hand, a phosphorescent material may utilize 75% of the triplet exited state and 25% of the singlet exited state, so it may theoretically reach 100% of the internal quantum efficiency. Accordingly, the phosphorescent light emitting material may have advantages of accomplishing around four times greater luminous efficiency than the fluorescent light emitting material.

SUMMARY

Embodiments are therefore directed to a compound for an optoelectronic device, an organic light emitting diode including the same, and a display including the organic light emitting diode.

The embodiments may be realized by providing a compound for an organic optoelectronic device in which substituents represented by the following Chemical Formulae 1 to 3 are sequentially combined:

[Chemical Formula 1]

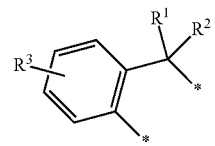

[Chemical Formula 2]

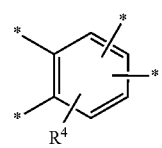

[Chemical Formula 3]

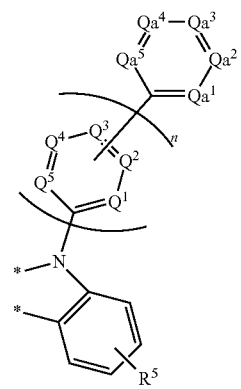

wherein, in Chemical Formulae 1 to 3 $Q^1$ to $Q^5$ and $Qa^1$ to $Qa^5$ are each independently N or CR, in which R is hydrogen, a substituted or unsubstituted C6 to C30 aryl group, a substituted or unsubstituted C3 to C30 heteroaryl group, or a combination thereof, $R^1$ to $R^5$ are each independently hydrogen, a substituted or unsubstituted carbazolyl group, a substituted or unsubstituted C1 to C30 alkyl group, a substituted or unsubstituted C6 to C30 aryl group, a substituted or unsubstituted C3 to C30 heteroaryl group, a substituted or unsubstituted C6 to C30 arylamine group, or a combination thereof, and n is an integer of 0 to 5.

The substituent represented by Chemical Formula 1 may be represented by the following Chemical Formula 1a:

[Chemical Formula 1a]

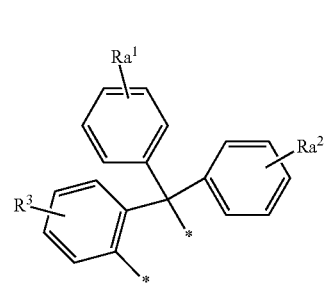

wherein, in Chemical Formula 1a $Ra^1$ and $Ra^2$ may each independently be hydrogen, a substituted or unsubstituted carbazolyl group, a substituted or unsubstituted C6 to C30 aryl group, a substituted or unsubstituted C6 to C30 arylamine group, or a combination thereof, and $R^3$ may be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof.

The substituent represented by Chemical Formula 2 may be represented by the following Chemical Formula 2a or 2b:

[Chemical Formula 2a]

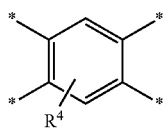

[Chemical Formula 2b]

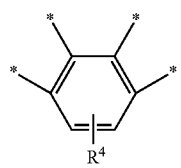

wherein, in Chemical Formulae 2a and 2b, $R^4$ may be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof.

In Chemical Formula 3, $Q^1$ to $Q^5$ and $Qa^1$ to $Qa^5$ may each independently be N or CR, provided that one or more of $Qa^1$, $Qa^3$, and $Qa^5$ is N, and remaining ones of $Qa^1$, $Qa^3$, and $Qa^5$ are each independently CR, in which R is hydrogen, a substituted or unsubstituted C6 to C30 aryl group, a substituted or unsubstituted C3 to C30 heteroaryl group, or a combination thereof.

$Q^1$ to $Q^5$ and $Qa^1$ to $Qa^5$ in Chemical Formula 3 may each independently be N or CR, provided that one to three selected from $Q^1$ to $Q^5$ is N, one to three selected from $Qa^1$ to $Qa^5$ is N, and remaining ones of $Q^1$ to $Q^5$ and $Qa^1$ to $Qa^5$ are each independently CR, in which R is hydrogen, a substituted or unsubstituted C6 to C30 aryl group, a substituted or unsubstituted C3 to C30 heteroaryl group, or a combination thereof.

n in Chemical Formula 3 may be an integer of 0 to 2.

The substituent represented by Chemical Formula 3 may be represented by the following Chemical Formula 3a:

[Chemical Formula 3a]

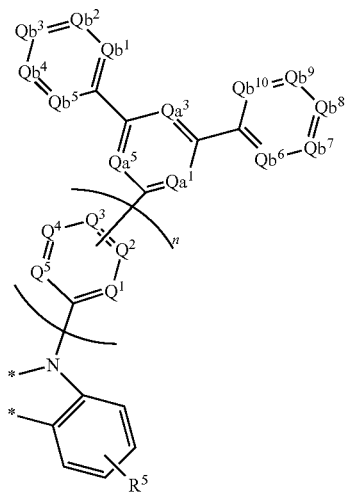

wherein, in Chemical Formula 3a $Qa^1$, $Qa^3$ and $Qa^5$ may each independently be N or CH, provided that one or more of $Qa^1$, $Qa^3$, and $Qa^5$ is N, $Q^1$ to $Q^5$ and $Qb^1$ to $Qb^{10}$ may each independently be N or CR, in which R is hydrogen, a substituted or unsubstituted C6 to C30 aryl group, a substituted or unsubstituted C3 to C30 heteroaryl group, or a combination thereof, $R^5$ may be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof, and n may be an integer of 0 to 5.

In Chemical Formulae 1 to 3, $R^3$ to $R^5$ may each independently be hydrogen, a C1 to C30 alkyl group, a C6 to C30 aryl group, or a combination thereof.

The compound for an organic photoelectric device may be represented by one of the following Chemical Formulae 4 to 9:

[Chemical Formula 4]

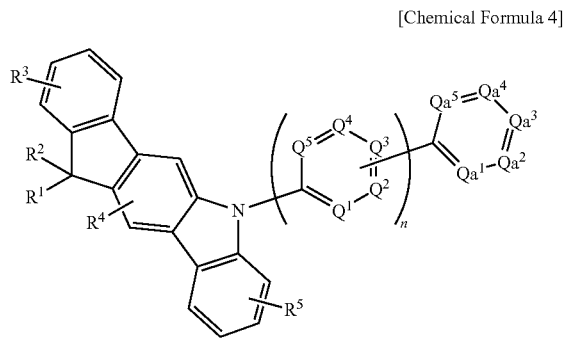

[Chemical Formula 5]

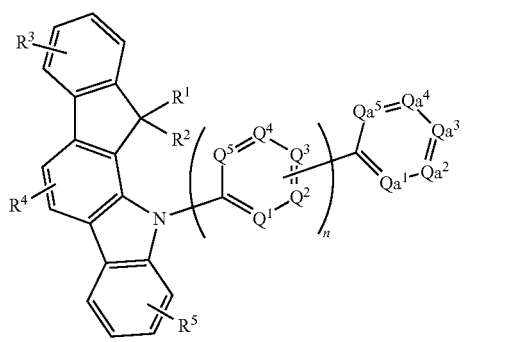

[Chemical Formula 6]

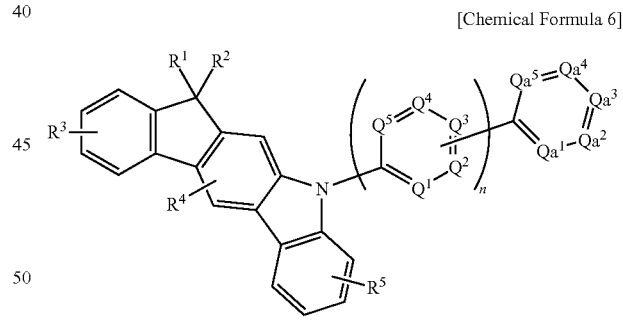

[Chemical Formula 7]

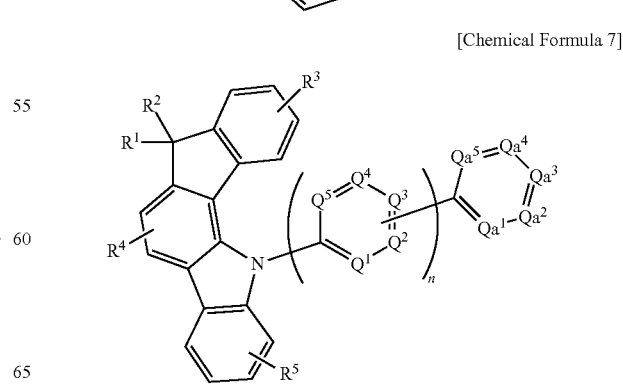

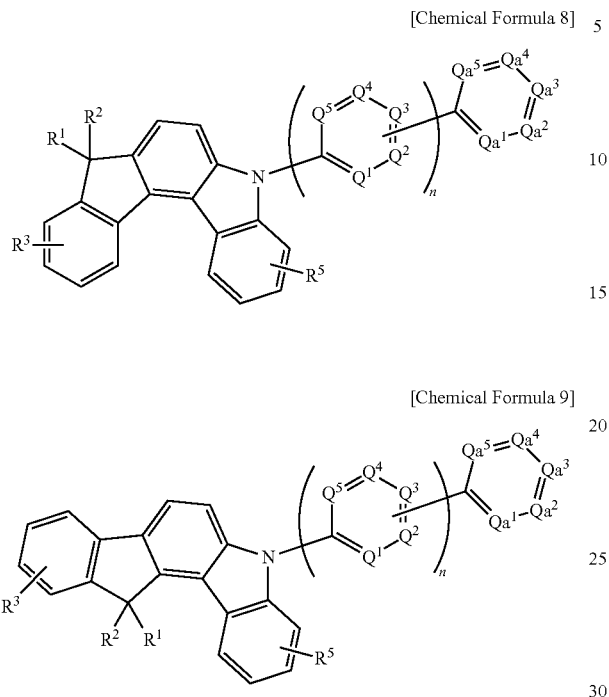

[Chemical Formula 8]

[Chemical Formula 9]

wherein, in Chemical Formulae 4 to 9 $Q^1$ to $Q^5$ and $Qa^1$ to $Qa^5$ may each independently be N or CR, in which R is hydrogen, a substituted or unsubstituted C6 to C30 aryl group, a substituted or unsubstituted C3 to C30 heteroaryl group, or a combination thereof, $R^1$ to $R^5$ may each independently be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof, and n may be an integer of 0 to 5.

The compound for an organic optoelectronic device may be represented by one of the following Chemical Formulae 10 to 33:

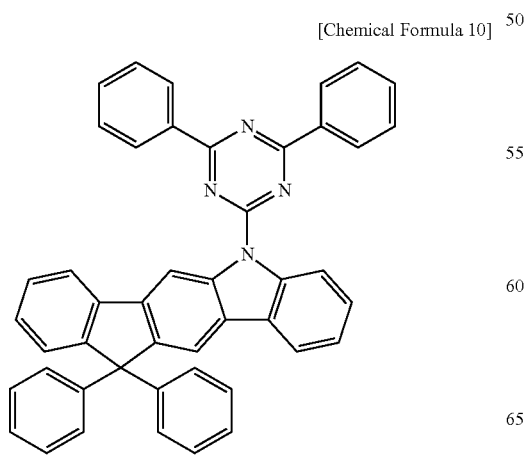

[Chemical Formula 10]

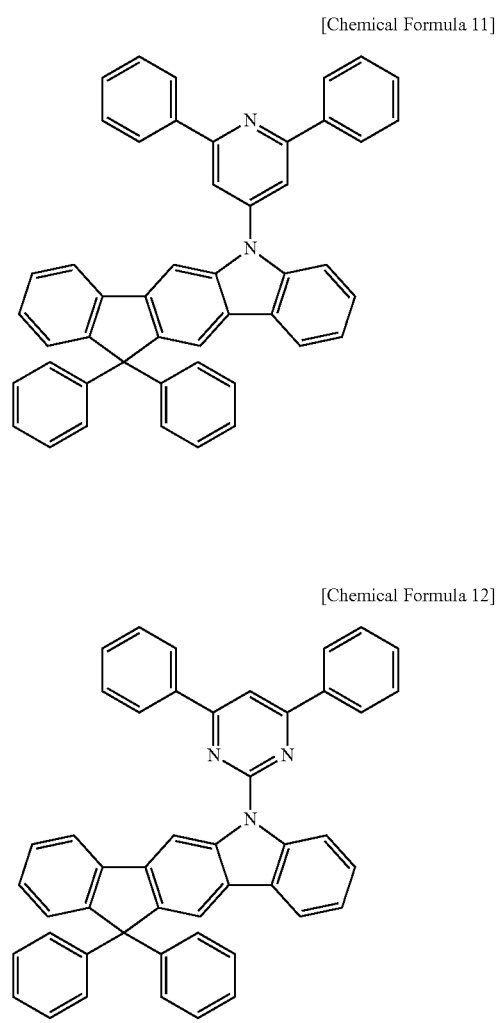

[Chemical Formula 11]

[Chemical Formula 12]

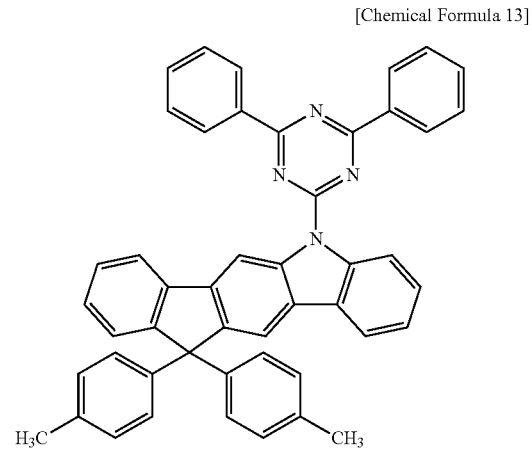

[Chemical Formula 13]

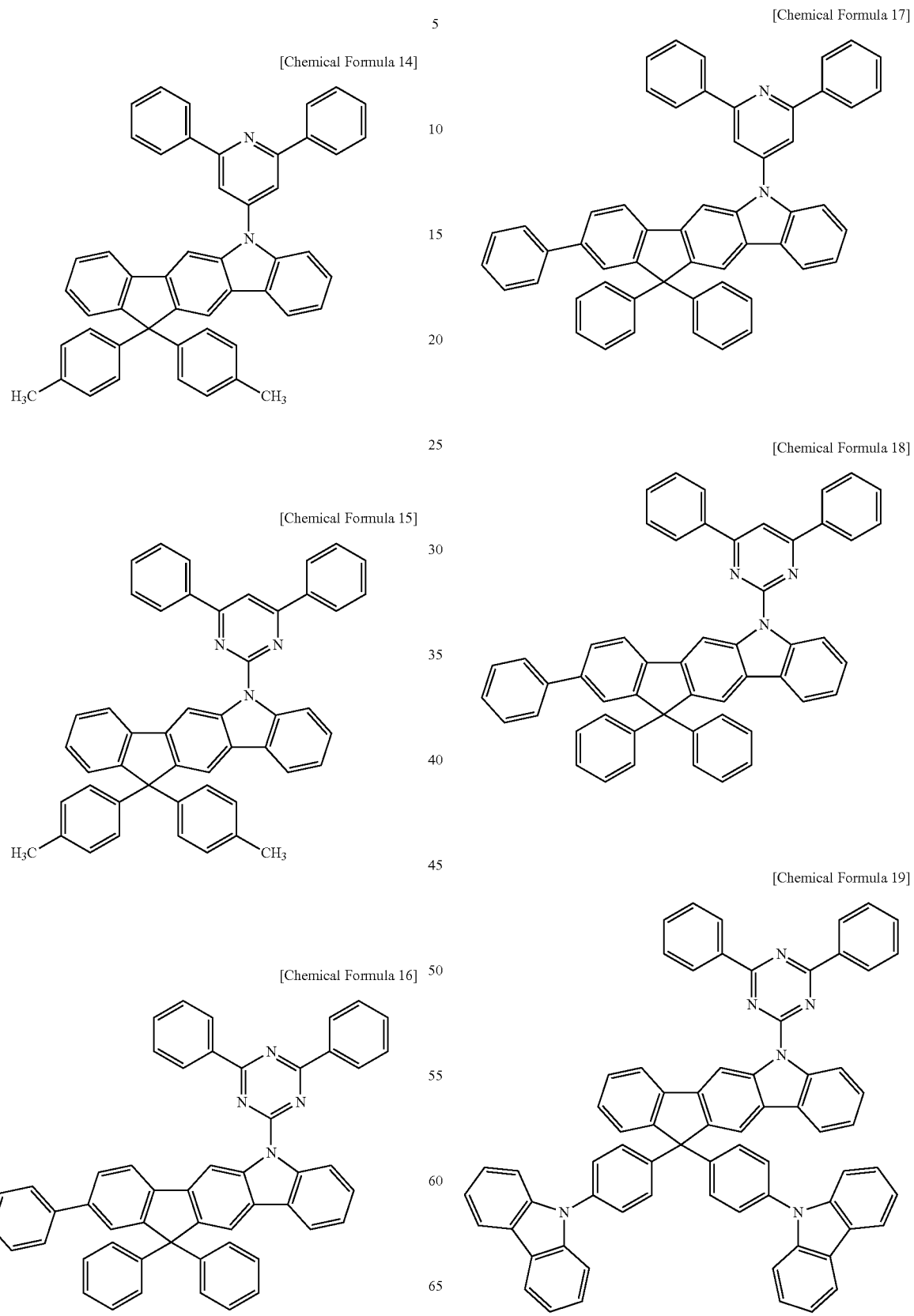

[Chemical Formula 20]
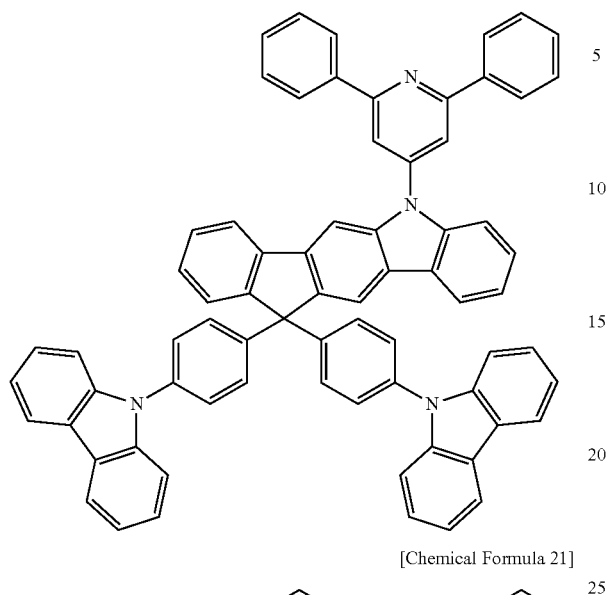
[Chemical Formula 21]
[Chemical Formula 22]
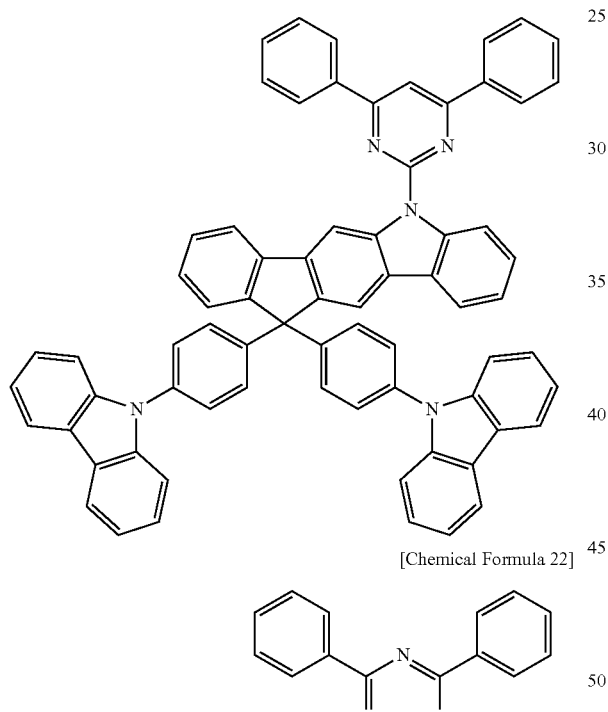
[Chemical Formula 23]
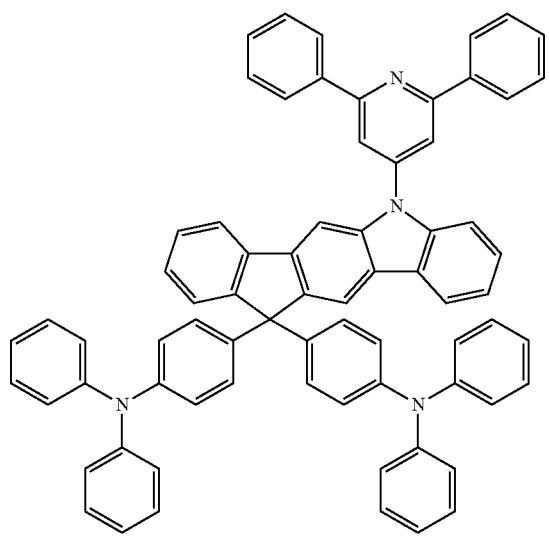
[Chemical Formula 24]
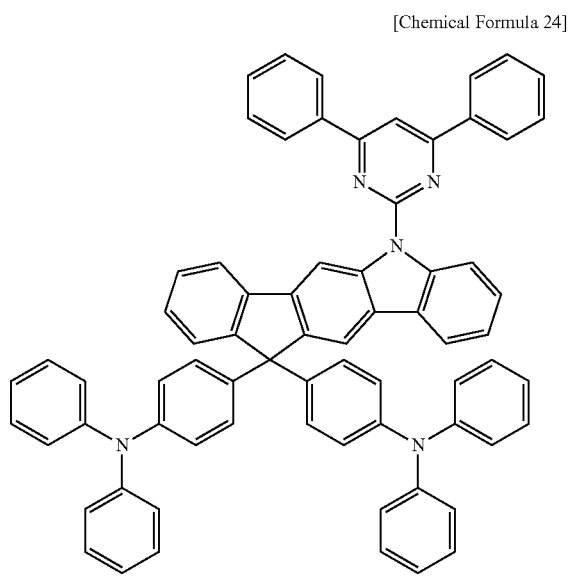
[Chemical Formula 25]
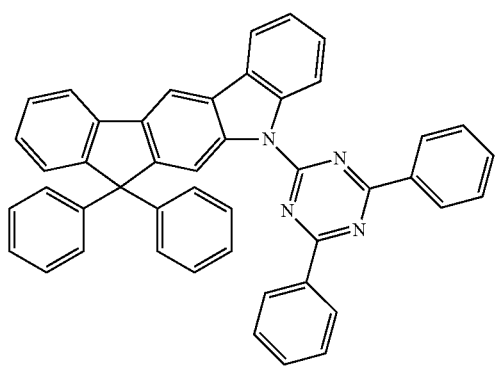

[Chemical Formula 26]
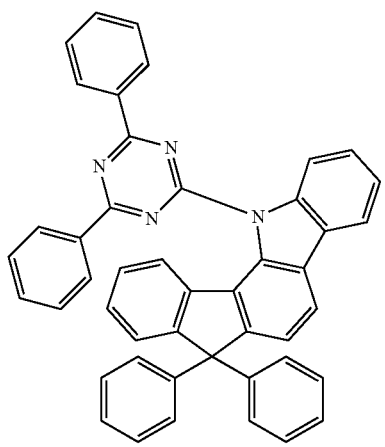
[Chemical Formula 27]
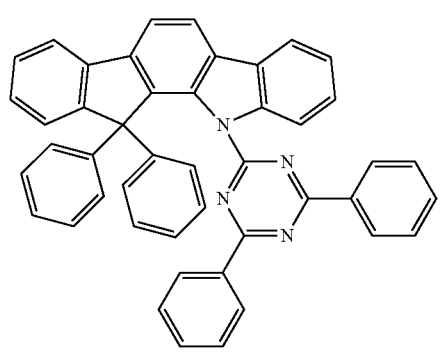
[Chemical Formula 28]
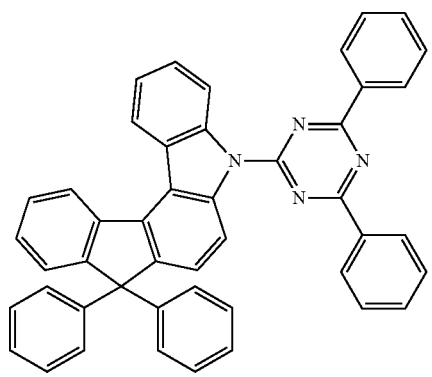
[Chemical Formula 29]
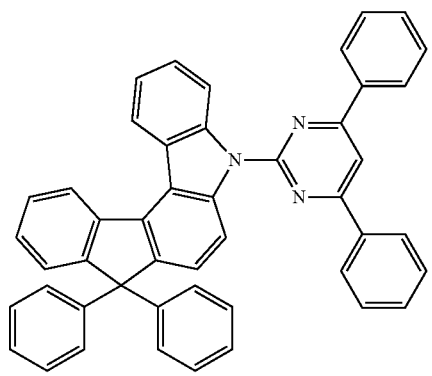
[Chemical Formula 30]
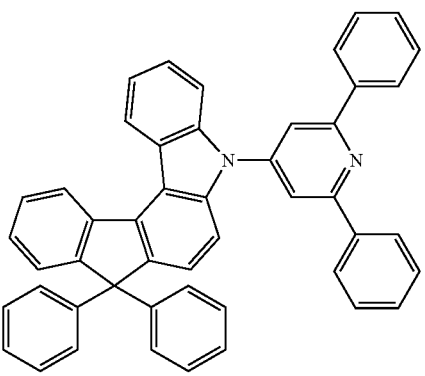
[Chemical Formula 31]
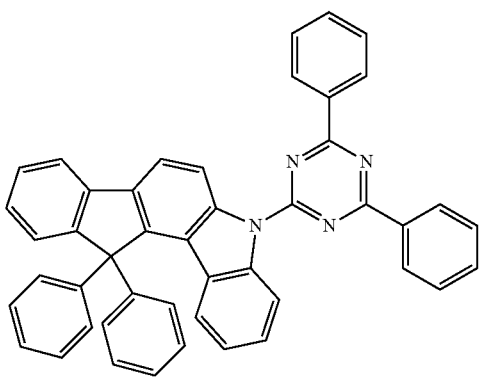
[Chemical Formula 32]
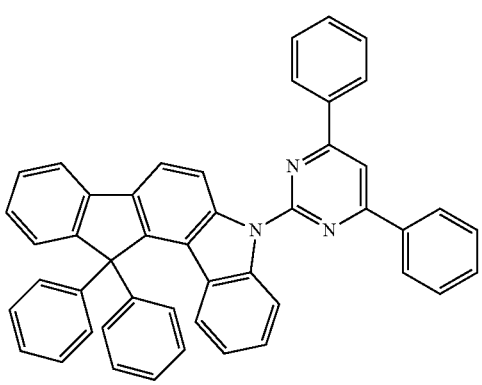
[Chemical Formula 33]
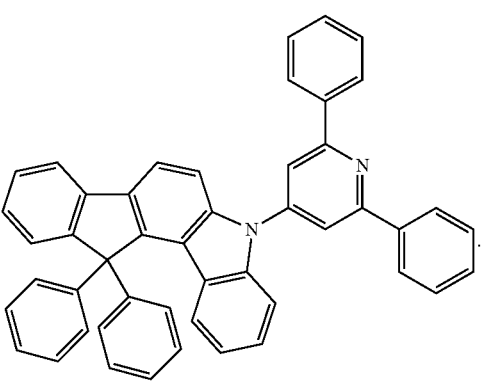
The compound for an organic optoelectronic device may be a charge transport material or a host material.

The compound for an organic optoelectronic device may have a thermal decomposition temperature (Td) of about 350 to about 600° C.

The embodiments may also be realized by providing an organic light emitting diode including an anode, a cathode, and at least one organic thin layer interposed between the anode and cathode, wherein the at least one organic thin layer includes the compound for an organic optoelectronic device according to an embodiment.

The at least one organic thin layer may include an emission layer, a hole blocking layer, an electron blocking layer, an electron transport layer (ETL), an electron injection layer (EIL), a hole injection layer (HIL), a hole transport layer (HTL), or a combination thereof.

The embodiments may also be realized by providing a display device including the organic light emitting diode according to an embodiment.

BRIEF DESCRIPTION OF THE DRAWINGS

The embodiments will become apparent to those of ordinary skill in the art by describing in detail exemplary embodiments with reference to the attached drawings, in which.

DETAILED DESCRIPTION

Figure 1:
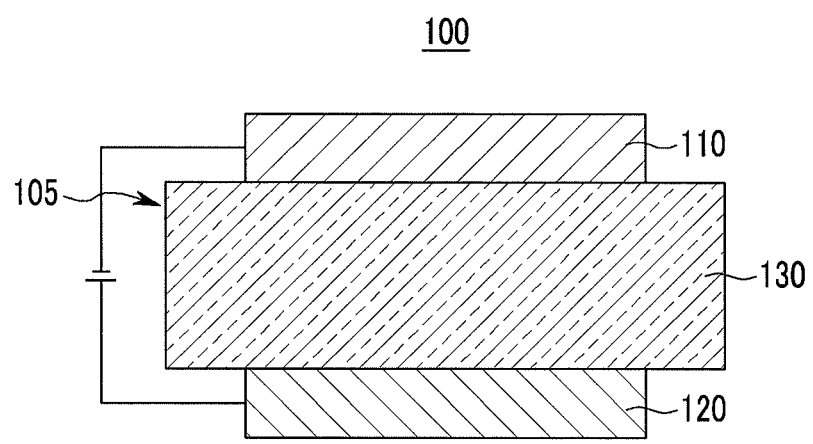
FIGS. 1 to 5 illustrate cross-sectional views showing organic light emitting diodes including compounds according to various embodiments.

Korean Patent Application No. 10-2009-0057234, filed on Jun. 25, 2009, in the Korean Intellectual Property Office, and entitled: "Compound for Organic Photoelectric Device and Organic Photoelectric Device Including the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

In the present specification, the term "substituted", when a definition is not otherwise provided, may refer to one substituted with a halogen group, a cyano group, a C1 to C30 alkyl group, a C3 to C30 cycloalkyl group, a C6 to C30 aryl group, a C1 to C30 alkoxy group, or a combination thereof.

In the present specification the term "halogen group", when a definition is not otherwise provided, may refer to a fluoro group, a chloro group, a bromo group, or a combination thereof.

In the present specification, the term "hetero", when a definition is not otherwise provided, may refer to one including 1 to 3 of N, O, S, P, and remaining carbons in one ring.

An embodiment provides a compound for an organic optoelectronic device in which substituents represented by the following Chemical Formulae 1 to 3 are sequentially combined.

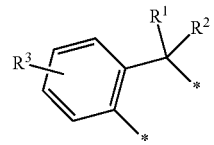

[Chemical Formula 1]

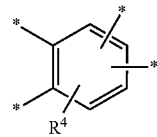

[Chemical Formula 2]

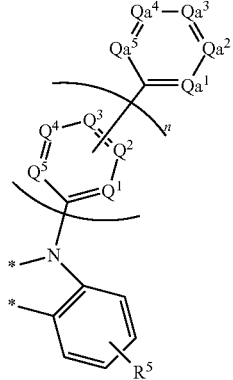

[Chemical Formula 3]

In Chemical Formulae 1 to 3, $Q^1$ to $Q^5$ and $Qa^1$ to $Qa^5$ may each independently be N or CR, in which R may be hydrogen, a substituted or unsubstituted C6 to C30 aryl group, a substituted or unsubstituted C3 to C30 heteroaryl group, or a combination thereof. In an implementation, when each $Q^1$ to $Q^5$ and $Qa^1$ to $Qa^5$ is independently CR, each R may be the same or different. In another implementation, when R is substituted with a C1 to C30 alkyl group, the compound may be applied to an organic thin layer of organic optoelectronic device and may help improve film formation characteristics of the organic thin layer. In Chemical Formulae 1 to 3, each * may represent an attachment point with a * of another of the Chemical Formulae. For example, two *s of Chemical Formula 1 may be attached at two *s of Chemical Formula 2, and two *s of Chemical Formula 3 may be attached at another two *s of Chemical Formula 2.

When R is a substituted or unsubstituted C6 to C30 aryl group, the aryl group may include a phenyl group, a naphthyl group, an anthracenyl group, a phenanthrenyl group, a tetracenyl group, a pyrenyl group, a fluorenyl group, or a combination thereof. However, the aryl group is not limited thereto.

When R is a substituted or unsubstituted C3 to C30 heteroaryl group, the heteroaryl group may include a thiophenyl, furanyl, pyrrolyl, imidazolyl, thiazolyl, oxazolyl, oxadiazolyl, thiadiazolyl, triazolyl, triazinyl, pyridinyl, pyrimidinyl, pyridazinyl, pyrazinyl, quinolinyl, isoquinolinyl, or a combination thereof. However, the heteroaryl group is not limited thereto.

$R^1$ to $R^5$ may each independently be hydrogen, a substituted or unsubstituted carbazolyl group, a substituted or unsubstituted C1 to C30 alkyl group, a substituted or unsubstituted C6 to C30 aryl group, a substituted or unsubstituted C3 to C30 heteroaryl group, a substituted or unsubstituted C6 to C30 arylamine group, or a combination thereof. n may be an integer of 0 to 5. When n is an integer of 2 or more, each repeating unit (i.e., the group including $Q^1$ to $Q^5$) may be the same or different.

The substituent represented by Chemical Formula 1 may be represented by the following Chemical Formula 1a.

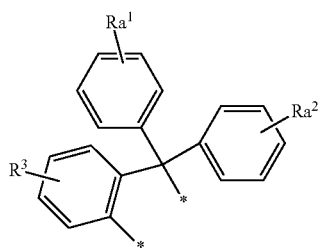

[Chemical Formula 1a]

In Chemical Formula 1a, $Ra^1$ and $Ra^2$ may each independently be hydrogen, a substituted or unsubstituted carbazolyl group, a substituted or unsubstituted C6 to C30 aryl group, a substituted or unsubstituted C6 to C30 arylamine group, or a combination thereof.

$R^3$ may be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof.

The substituent represented by Chemical Formula 2 may be represented by the following Chemical Formula 2a or 2b.

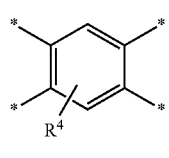

[Chemical Formula 2a]

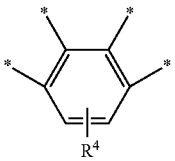

[Chemical Formula 2b]

In Chemical Formulae 2a and 2b, $R^4$ may be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof.

As described above, $Q^1$ to $Q^5$ and $Qa^1$ to $Qa^5$ in the above Chemical Formula 3 may each independently be N or CR. In an implementation, at least one selected from $Q^1$ to $Q^5$ and $Qa^1$ to $Qa^5$ may be N, and remaining ones of $Q^1$ to $Q^5$ and $Qa^1$ to $Qa^5$ may each independently be CR, in which R may be hydrogen, a substituted or unsubstituted C6 to C30 aryl group, a substituted or unsubstituted C3 to C30 heteroaryl group, or a combination thereof. For example, one to three selected from $Q^1$ to $Q^5$ may be N, one to three selected from $Qa^1$ to $Qa^5$ may be N, and remaining ones of $Q^1$ to $Q^5$ and $Qa^1$ to $Qa^5$ may each independently be CR, in which R may be hydrogen, a substituted or unsubstituted C6 to C30 aryl group, a substituted or unsubstituted C3 to C30 heteroaryl group, or a combination thereof. Accordingly, the compound may include a substituent that functions effectively as an electron transporting group.

In an implementation, in the above Chemical Formula 3, n may be an integer of 0 to 2.

The substituent represented by Chemical Formula 3 may be represented by the following Chemical Formula 3a.

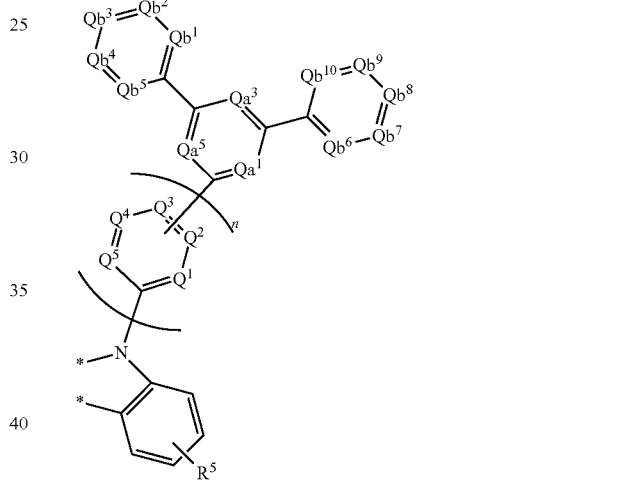

[Chemical Formula 3a]

In Chemical Formula 3a, $Qa^1$, $Qa^3$, and $Qa^5$ may each independently be N or CH. In an implementation, one or more of $Qa^1$, $Qa^3$, and $Qa^5$ may be N.

$Q^1$ to $Q^5$ and $Qb^1$ to $Qb^{10}$ may each independently be N or CR, in which R may be hydrogen, a substituted or unsubstituted C6 to C30 aryl group, a substituted or unsubstituted C3 to C30 heteroaryl group, or a combination thereof.

$R^5$ may be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof.

n may be an integer of 0 to 5.

In Chemical Formulae 1 to 3, $R^3$ to $R^5$ may each independently be hydrogen, a C1 to C30 alkyl group, a C6 to C30 aryl group, or a combination thereof.

The compound for an organic optoelectronic device including the substituents represented by Chemical Formulae 1 to 3 may be represented by one of the following Chemical Formulae 4 to 9.

[Chemical Formula 4]

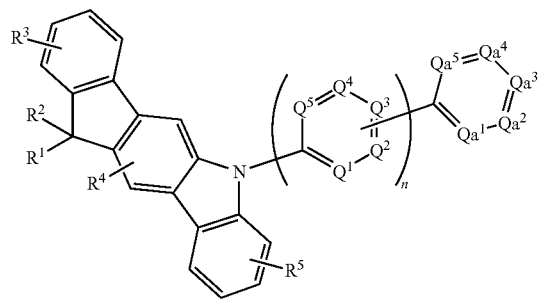

[Chemical Formula 9]

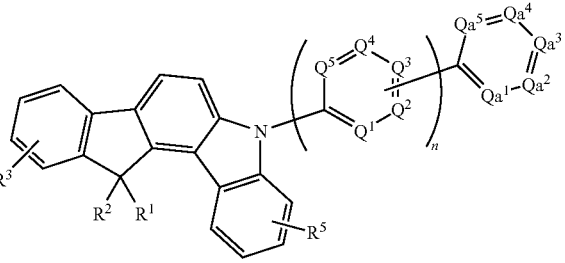

[Chemical Formula 5]

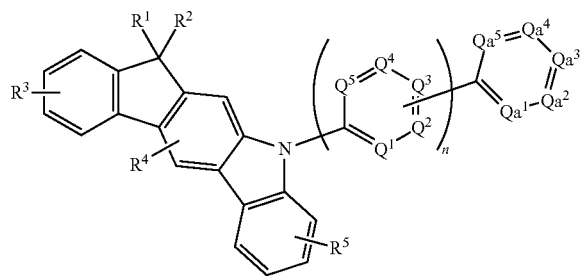

In Chemical Formulae 4 to 9, $Q^1$ to $Q^5$ and $Qa^1$ to $Qa^5$ may each independently be N or CR, in which R may be hydrogen, a substituted or unsubstituted C6 to C30 aryl group, a substituted or unsubstituted C3 to C30 heteroaryl group, or a combination thereof.

$R^1$ to $R^5$ may each independently be hydrogen, a substituted or unsubstituted carbazolyl group, a substituted or unsubstituted C6 to C30 aryl group, a substituted or unsubstituted C3 to C30 heteroaryl group, a substituted or unsubstituted C6 to C30 arylamine group, or a combination thereof.

n may be an integer of 0 to 5.

In an implementation, the compound for an organic optoelectronic device including the substituents represented by Chemical Formulae 1 to 3 may be represented by one of the following Chemical Formulae 10 to 33. However, the compound for an organic optoelectronic device according to the embodiments is not limited thereto.

[Chemical Formula 6]

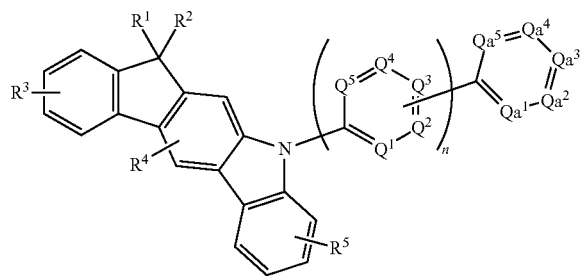

[Chemical Formula 10]

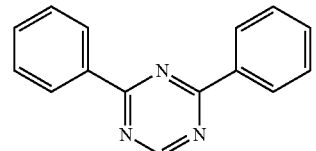

[Chemical Formula 7]

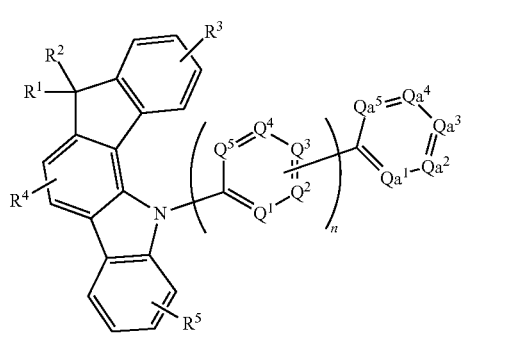

[Chemical Formula 11]

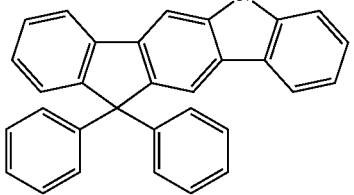

[Chemical Formula 8]

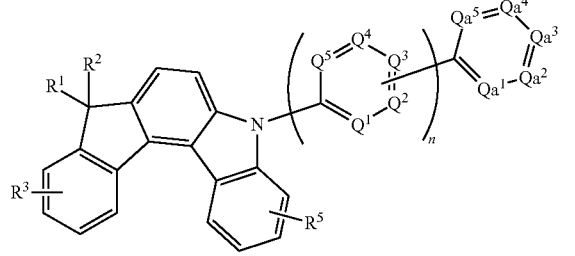

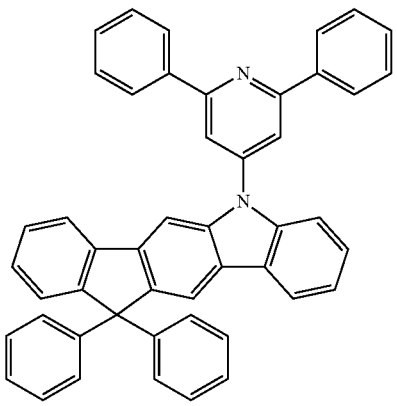

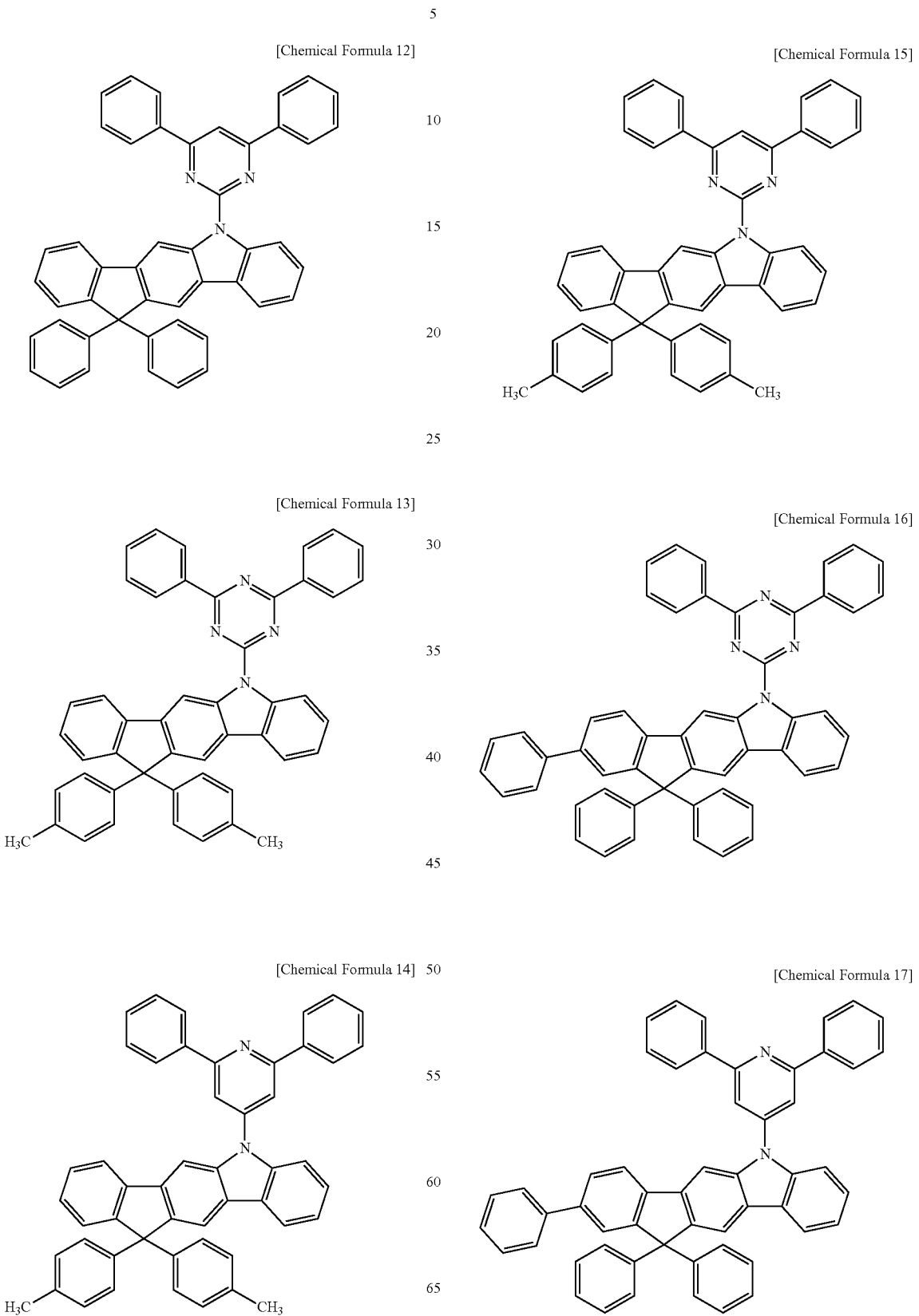

[Chemical Formula 18]
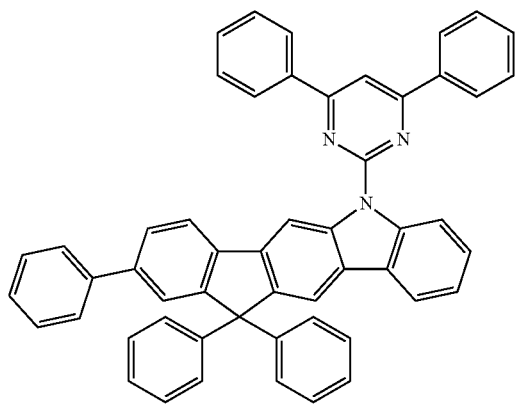
[Chemical Formula 19]
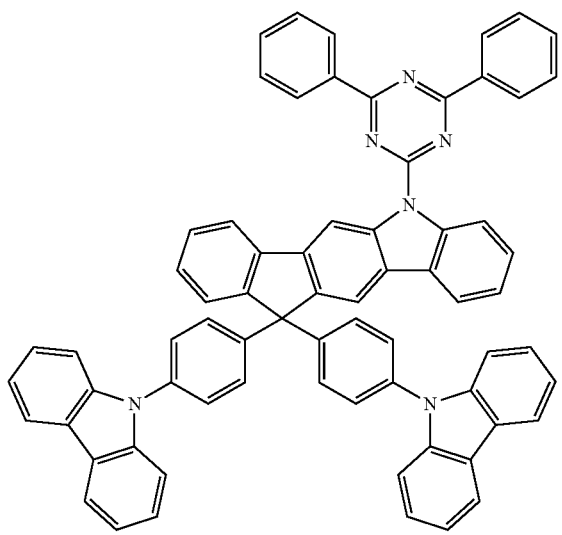
[Chemical Formula 20]
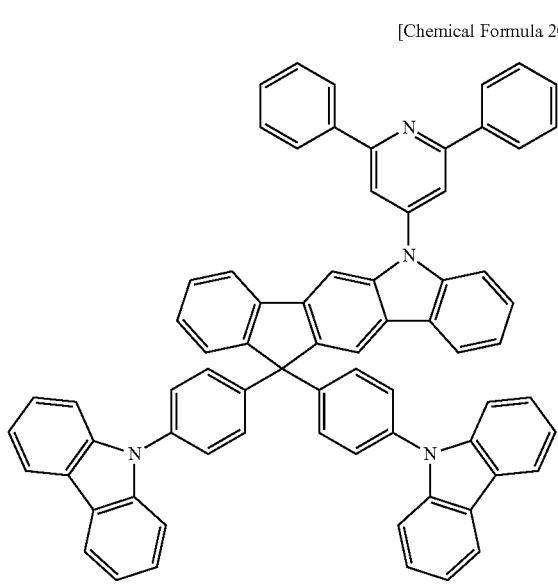
[Chemical Formula 21]
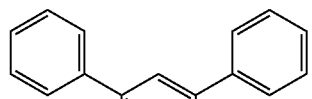
[Chemical Formula 22]
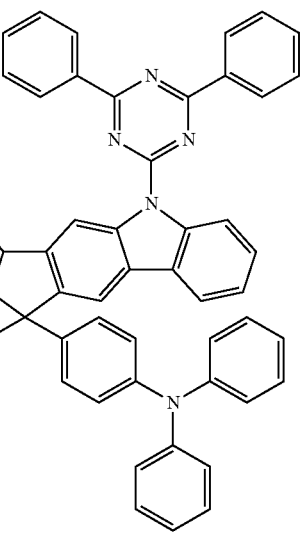
[Chemical Formula 23]
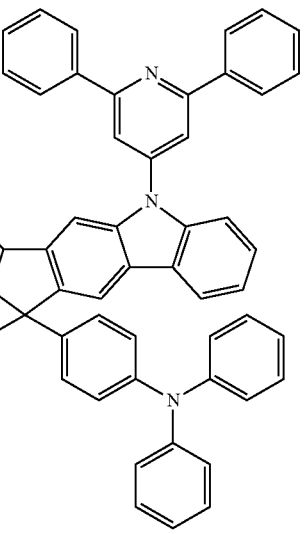

[Chemical Formula 24]
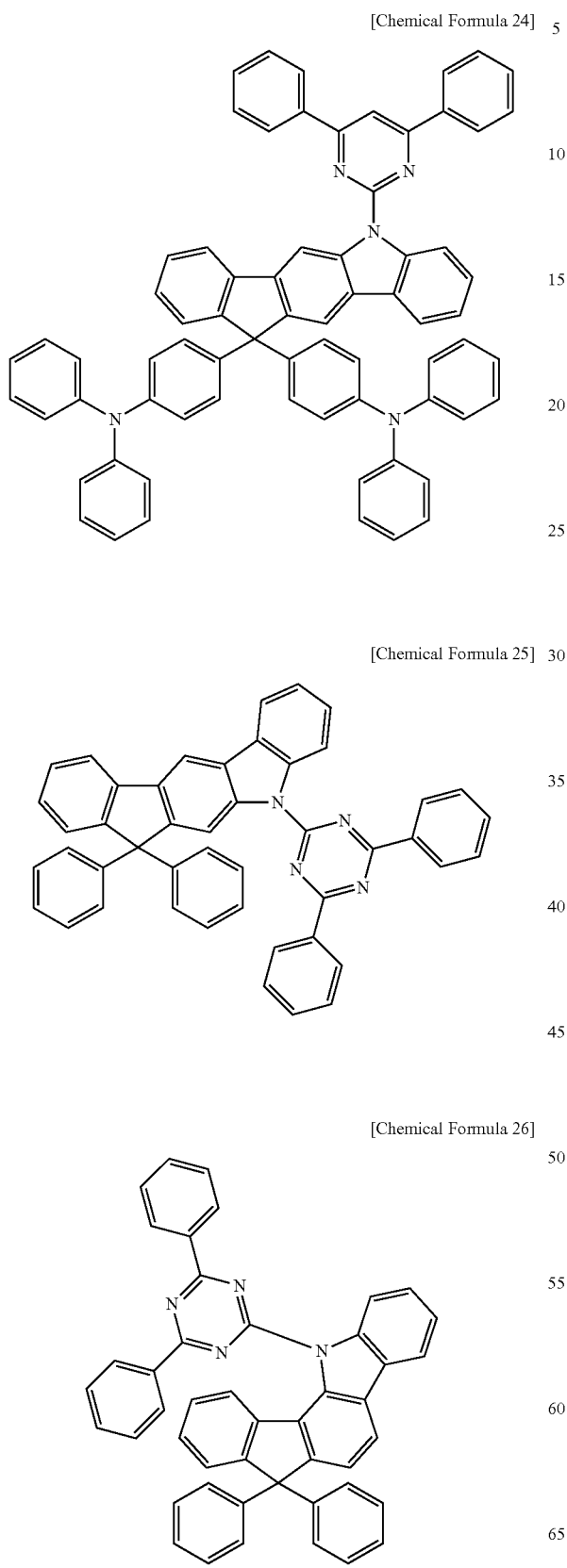
[Chemical Formula 25]
[Chemical Formula 26]
[Chemical Formula 27]
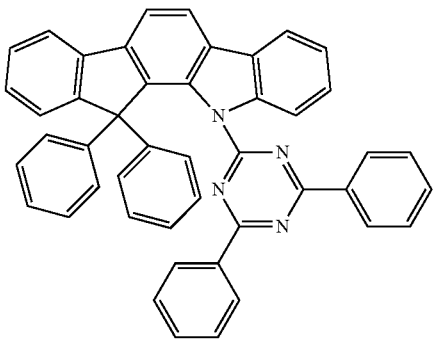
[Chemical Formula 28]
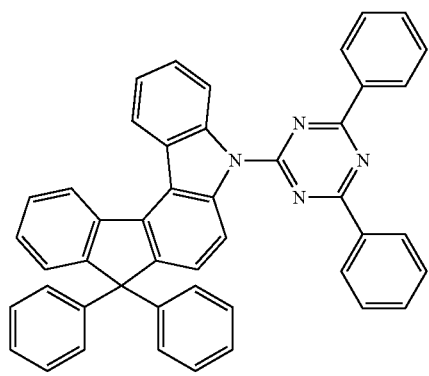
[Chemical Formula 29]
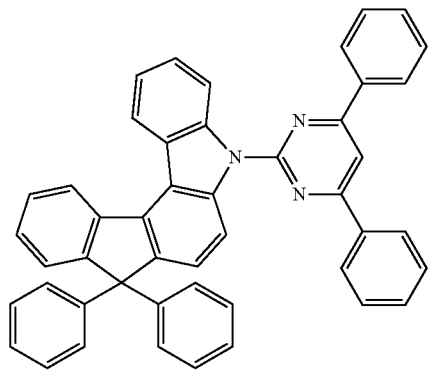
[Chemical Formula 30]
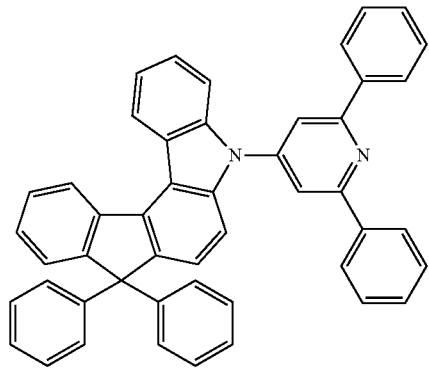

-continued

[Chemical Formula 31]

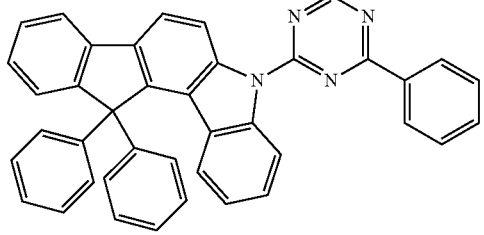

[Chemical Formula 32]

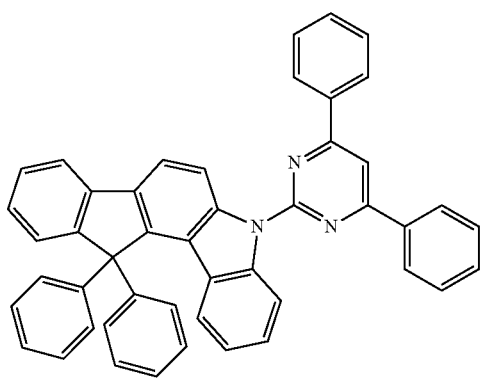

[Chemical Formula 33]

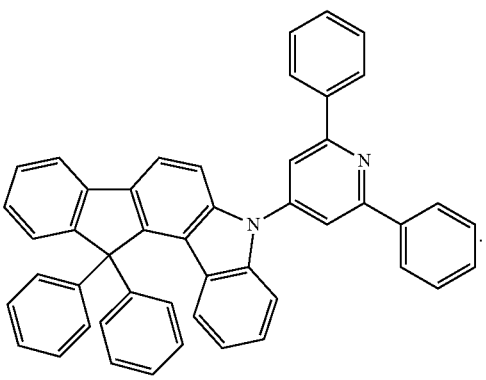

The compound for an organic optoelectronic device may be, or may be used as, a charge transport material or a host material. In an implementation, when the compound for an organic optoelectronic device is used as a host material, the compound may be a phosphorescent host material that may help lower a driving voltage and may help improve luminous efficiency of an organic optoelectronic device.

When the compound for an organic optoelectronic device is a host material, the compound for an organic optoelectronic device may be used as a mixture or blend with a suitable low molecular weight host material or a polymer host material. In addition, a binder resin, e.g., polyvinylcarbazole, polycarbonate, polyester, poly arylate, polystyrene, acryl polymer, methacryl polymer, polybutyral, polyvinylacetal, a diallylphthalate polymer, phenolic resin, an epoxy resin, a silicone resin, polysulfone resin, or a urea resin, may be mixed therewith.

For example, the low molecular weight host material may include a compound represented by one of the following Chemical Formulae 34 to 37. The polymer host material may include a polymer having a conjugated double bond, e.g., a fluorene-based polymer, a polyphenylenevinylene-based polymer, a polyparaphenylene-based polymer, or the like. However, the low molecular weight host material and polymer host material are not limited thereto.

[Chemical Formula 34]

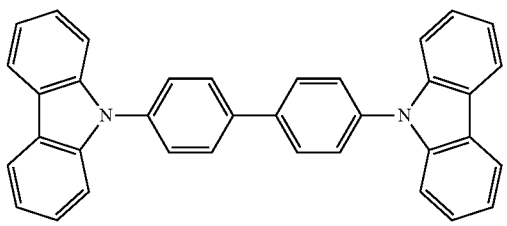

[Chemical Formula 35]

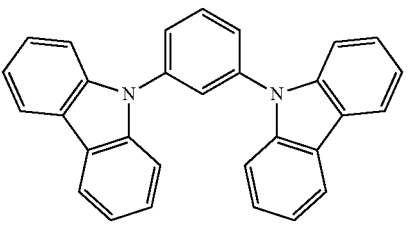

[Chemical Formula 36]

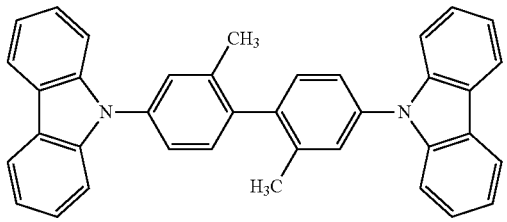

[Chemical Formula 37]

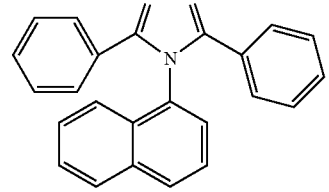

When the compound for an organic optoelectronic device is used as a host material, the compound for an organic optoelectronic device may be used singularly, or along with a dopant. The dopant may be a compound having a high emission property, by itself. However, the dopant may be added to the host in a minor amount, and may also be referred to as a guest. The dopant may be a light-emitting material while being doped in a host material. In an implementation, the dopant may include, e.g., a metal complex capable of light-emitting by multiplet excitations such as triplet excitation or more. Such a dopant may include a red (R), green (G), blue (B), and/or white (W) fluorescent or phosphorescent dopant, e.g., a red, green, blue, and/or white phosphorescent dopant. The dopant may include a material that has high luminous efficiency, is not agglomerated, and is uniformly distributed in a host material.

The phosphorescent dopant may include an organic metal compound including an element, e.g., Ir, Pt, Os, Ti, Zr, Hf, Eu, Tb, Tm, Fe, Co, Ni, Ru, Rh, Pd, or a combination thereof. For example, a red phosphorescent dopant may include platinum-octaethylporphyrin complex (PtOEP), Ir(btp)$_2$(acac) (bis(2-(2'-benzothienyl)-pyridinato-N,C3')iridium(acetylacetonate)), Ir(Piq)$_2$(acac), Ir(Piq)$_3$, RD61 (UDC), and the like. A green phosphorescent dopant may include Ir(PPy)$_2$(acac), Ir(PPy)$_3$, GD48 (UDC), and the like. A blue phosphorescent dopant may include (4,6-F$_2$PPy)$_2$Irpic, fIrpic(Ir bis[4,6-difluorophenyl)-pyridinato-N,C2']picolinate), and the like. The "Piq" denotes 1-phenylisoquinoline, "acac" denotes acetylacetonate, and PPy denotes 2-phenylpyridine.

The compound for an organic optoelectronic device according to an embodiment may have a thermal decomposition temperature (Td) of about 350 to about 600° C. Accordingly, the compound for an organic optoelectronic device may have excellent thermal stability and may be used as a host material or a charge transport material. Therefore, life-span of the organic optoelectronic device may be improved.

Another embodiment provides an organic optoelectronic device including an anode, a cathode, and an organic thin layer between the anode and the cathode. The organic thin layer may include the compound for an organic optoelectronic device according to an embodiment. The organic optoelectronic device may include, e.g., an organic photoelectronic device, an organic light emitting diode, an organic solar cell, an organic transistor, organic photo conductor drum, an organic memory device, and the like. In an organic solar cell, the compound for an organic optoelectronic device according to an embodiment may be applied to an electrode or an electrode buffer layer of the organic solar cell to help improve quantum efficiency. In an implementation, the compound according to an embodiment may be applied to an electrode material of a gate, source-drain electrodes, and the like, of an organic transistor.

The organic thin layer including the compound for an organic optoelectronic device may include an emission layer, a hole blocking layer, an electron blocking layer, an electron transport layer (ETL), an electron injection layer (EIL), a hole injection layer (HIL), a hole transport layer (HTL), or a combination thereof.

Hereinafter, an organic light emitting diode is illustrated in more detail.

FIGS. 1 to 5 illustrate cross-sectional views showing organic light emitting diodes including the compound for an organic optoelectronic device according to an embodiment.

Referring to FIGS. 1 to 5, the light emitting diodes 100, 200, 300, 400, and 500 according to an embodiment may include at least one organic thin layer 105 interposed between an anode 120 and a cathode 110.

A substrate of an organic photoelectric device is not particularly limited, and may include a glass substrate or a transparent plastic substrate having excellent transparency, surface smoothness, handling ease, and water repellency.

The anode 120 may include an anode material laving a large work function in order to facilitate hole injection into an organic thin layer. The anode material may include, e.g., a metal such as nickel, platinum, vanadium, chromium, copper, zinc, gold, or the like, or an alloy of the foregoing metals; metal oxide such as zinc oxide, indium oxide, indium tin oxide (ITO), indium zinc oxide (IZO), or the like; and/or a combined metal and oxide such as ZnO/Al, SnO$_2$/Sb, or the like. However, the anode material is not limited thereto. In an implementation, the anode may include a transparent electrode including ITO.

The cathode 110 may include a cathode material having a small work function in order to facilitate electron injection into an organic thin layer. The cathode material may include, e.g., a metal such as magnesium, calcium, sodium, potassium, titanium, indium, yttrium, lithium, gadolinium, aluminum, silver, tin, lead, cesium, barium, or the like, or alloys thereof; or a multi-layered material such as LiF/Al, LiO$_2$/Al, LiF/Ca, LiF/Al, BaF$_2$/Ca, or the like. The cathode material is not limited thereto. In an implementation, the cathode may include a metal electrode such as aluminum.

Referring to FIG. 1, the organic light emitting diode 100 may include an organic thin layer 105 including only an emission layer 130.

Figure 2:
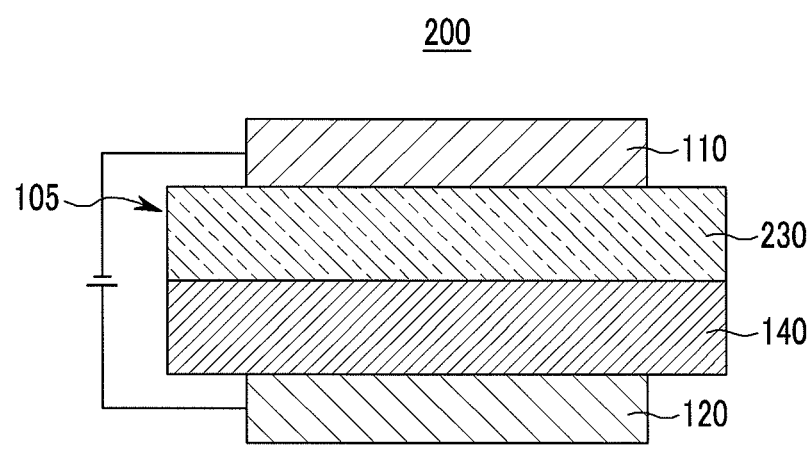

Referring to FIG. 2, a double-layered organic light emitting diode 200 may include an organic thin layer 105 including an emission layer 230 (including an electron transport layer (ETL)) and a hole transport layer (HTL) 140. The emission layer 230 may also function as an electron transport layer (ETL), and the hole transport layer (HTL) 140 layer may have excellent binding properties with a transparent electrode such as ITO (e.g., the anode 120) and/or may have excellent hole transporting properties.

The hole transport layer (HTL) 140 may include any suitable hole transport material, e.g., poly(3,4-ethylenedioxythiophene) (PEDOT) doped with poly(styrenesulfonate) (PSS) (PEDOT:PSS), N,N'-bis(3-methylphenyl)-N,N-diphenyl-[1,1'-biphenyl]-4,4'-diamine (TPD), N,N'-di(1-naphthyl)-N,N'-diphenylbenzidine (NPB) and the like, along with the compound for an organic optoelectronic device according to an embodiment. However, the hole transport material is not limited thereto.

Figure 3:
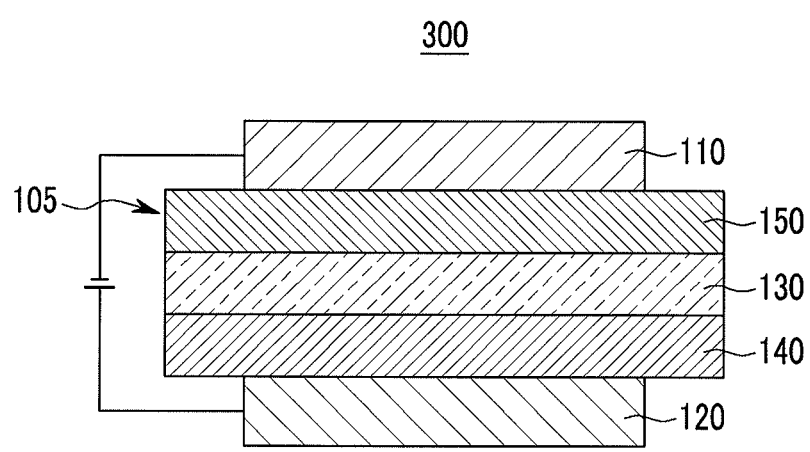

Referring to FIG. 3, a three-layered organic light emitting diode 300 may include an organic thin layer 105 including an electron transport layer (ETL) 150, an emission layer 130, and a hole transport layer (HTL) 140. The emission layer 130 may be independently installed, and layers having excellent electron transporting properties and excellent hole transporting properties may be separately stacked.

The electron transport layer (ETL) 150 may include any suitable electron transport material, e.g., aluminum tris(8-hydroxyquinoline) (Alq$_3$); a 1,3,4-oxadiazole derivative such as 2-(4-biphenyl-5-phenyl-1,3,4-oxadiazole (PBD); a quinoxalin derivative such as 1,3,4-tris[(3-phenyl-6-trifluoromethyl)quinoxalin-2-yl]benzene (TPQ); and a triazole derivative, along with the compound for an organic optoelectronic device according to an embodiment. However, the electron transport material is not limited thereto.

Figure 4:
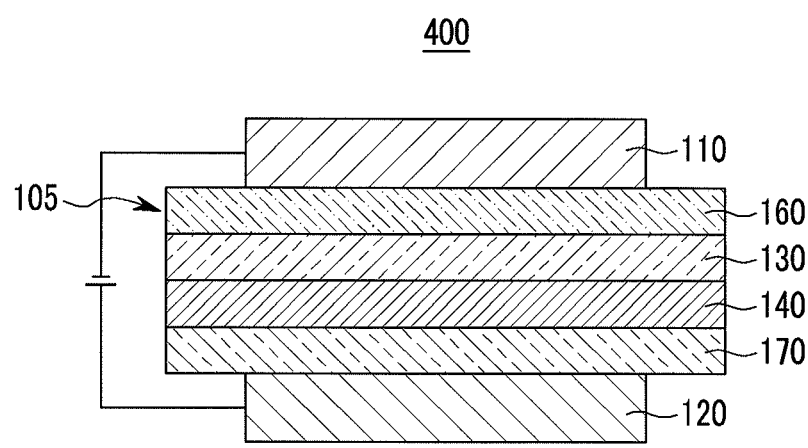

FIG. 4 illustrates a four-layered organic light emitting diode 400 that includes an organic thin layer 105 including an electron injection layer (EIL) 160, an emission layer 130, a hole transport layer (HTL) 140, and a hole injection layer (HIL) 170 (for binding with the anode 120 of ITO).

Figure 5:
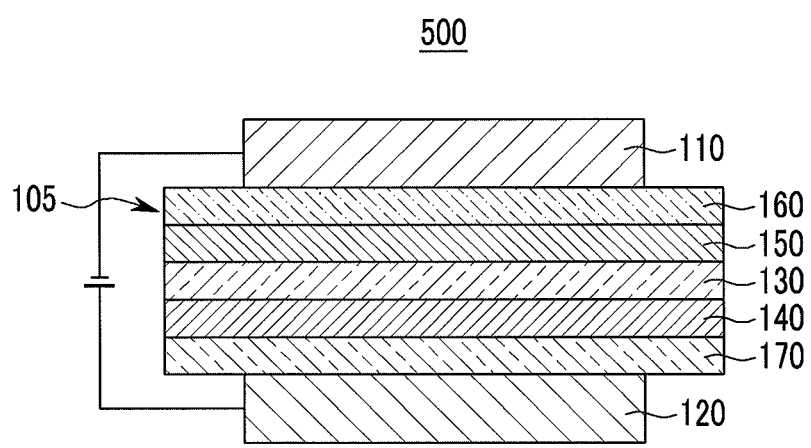

FIG. 5 illustrates a five layered organic light emitting diode 500 that includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

The emission layers 130 and 230 may have a thickness of about 5 to about 1,000 nm, and the hole transport layer (HTL) 140 and electron transport layer (ETL) 150 may each have a thickness of about 10 to about 10,000 Å. However, the thicknesses are not limited thereto.

In FIGS. 1 to 5, the organic thin layer 105 (selected from the electron transport layer (ETL) 150, electron injection layer (EIL) 160, emission layer 130 and 230, hole transport layer (HTL) 140, hole injection layer (HIL) 170, and/or a combination thereof) may include the compound for an organic optoelectronic device according to an embodiment. The material for the organic light emitting diode may be used for an electron transport layer (ETL) 150, a hole transport layer (HTL) 140, and/or electron injection layer (EIL) 160.

When the compound is used for the electron transport layer (ETL), it is possible to provide an organic light emitting diode having a simpler structure because an additional or separate hole blocking layer may be omitted.

Furthermore, when the compound for an organic optoelectronic device is included in the emission layer 130 and 230, the material for the organic light emitting diode may be included as a phosphorescent host, and the emission layer 130 and 230 may further include a dopant. In an implementation, the dopant may include a red, green, blue, and/or white phosphorescent dopant.

The organic light emitting diode may be fabricated by: forming an anode on a substrate, forming an organic thin layer (by a dry coating method such as evaporation, sputtering, plasma plating, and ion plating, or a wet coating method such as spin coating, dipping, and flow coating); and providing a cathode thereon.

Another embodiment provides a display device including the organic light emitting diode.

The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

Synthesis of Compound for Organic Optoelectronic Device

EXAMPLE 1

A compound for an organic optoelectronic device was synthesized according to the following Reaction Scheme 1.

First Step: Synthesis of Intermediate Product (B)

11.0 g (24.7 mmol) of a compound A, 6.0 g (29.7 mmol) of 1-bromo-2-nitro benzene, 1 g (0.86 mmol) of tetrakis(triphenylphosphine)palladium were dissolved in 200 mL of tetrahydrofuran (THF) in a 500 mL round-bottomed flask with a thermometer, a reflux-condenser, and an agitator under an argon atmosphere, and 50 mL of 2M potassium carbonate was added thereto. The mixture was agitated at 75° C. for 24 hours.

The agitated reactant was cooled down to room temperature to complete the reaction and then, extracted with methylene chloride and cleaned with water. Next, the reactant was treated with anhydrous magnesium sulfate to remove moisture and filtered to remove an organic solvent therefrom. The final residue was purified through silica gel chromatography using a mixed solvent prepared by mixing methylene chloride and hexane in a volume ratio of 1:1, obtaining 9 g of an intermediate product (B) (yield: 82.7%).

Second Step: Synthesis of Intermediate Product (C)

8 g (18.2 mmol) the intermediate product (B) synthesized in the first step and 14.3 g (54.6 mmol) of triphenylphosphine were dissolved in 150 ml of dichlorobenzene. The solution was heated and refluxed at 160° C. under an argon atmosphere.

The reactant was extracted with methylenechloride and cleaned with water, after the organic solvent therein was distilled and removed under reduced pressure. Then, the reactant was treated with anhydrous magnesium sulfate to remove moisture and filtered to remove an organic solvent therein. The final residue was purified through silica gel chromatography using a mixed solvent prepared by mixing methylenechloride and hexane in a volume ratio of 2:1, obtaining 5.3 g of an intermediate product (C) (yield: 71.5%).

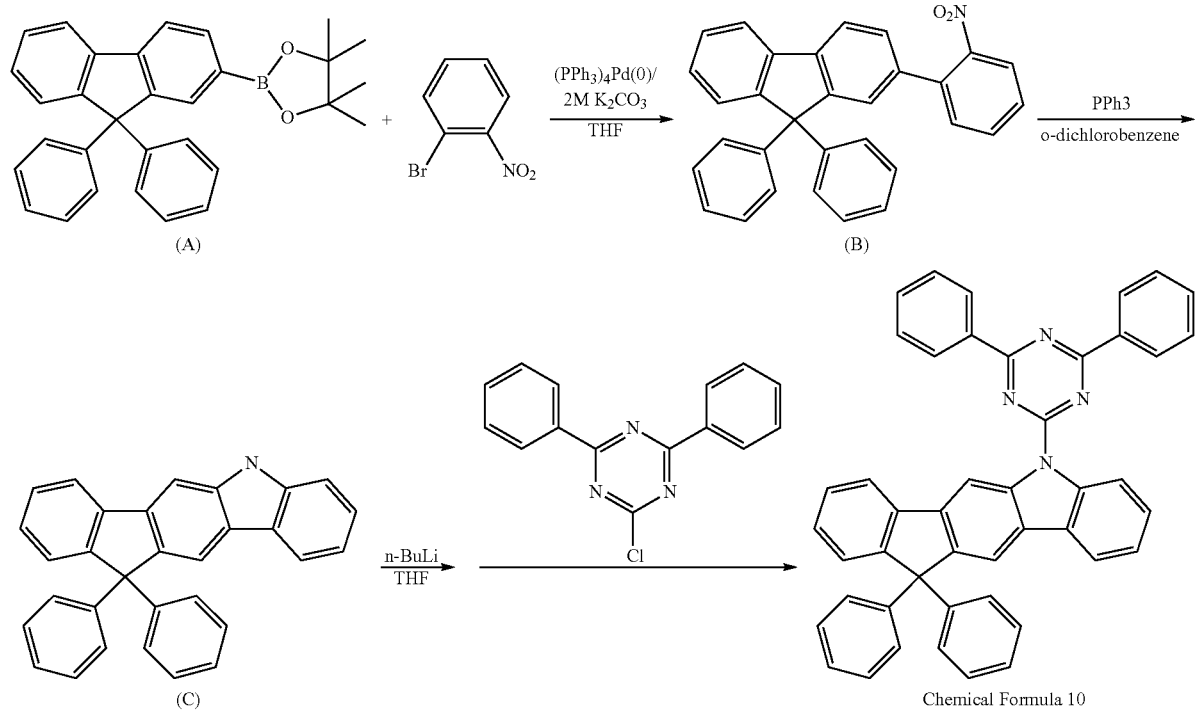

[Reaction Scheme 1]

Chemical Formula 10

Third Step: Synthesis of Compound for Organic Photoelectric Device 5 g (12.2 mmol) of the intermediate product (C) (synthesized in the second step) was dissolved in 100 mL of anhydrous tetrahydrofuran (THF), and 9.2 mL of 1.6 M n-BuLi was added in a dropwise fashion at −78° C. The mixture was slowly agitated for 30 minutes. Next, the reactant was further agitated at a room temperature for 20 minutes and then, mixed with 3.59 g (13.4 mmol) of 2-chloro-4,6-diphenyl triazine at −78° C. The mixture was agitated at room temperature for 12 hours.

The agitated reactant was brought to room temperature to complete the reaction and then, extracted with methylene chloride and cleaned with water. Then, the resulting reactant was treated with anhydrous magnesium sulfate to remove moisture and filtered to remove an organic solvent therefrom. The final residue was purified and recrystallized through silica gel chromatography using a mixed solvent prepared by mixing methylene chloride and hexane in a volume ratio of 1:3, obtaining 4 g of a compound (Chemical Formula 10) for an organic optoelectronic device (yield: 51.3%).

Atomic analysis was performed on the compound for an organic optoelectronic device.

Calcd: C, 86.49; H, 4.73; N, 8.77
Found: C, 86.50; H, 4.72; N, 8.77

EXAMPLE 2

A compound for an organic optoelectronic device was synthesized according to the following Reaction Scheme 2.

[Reaction Scheme 2]

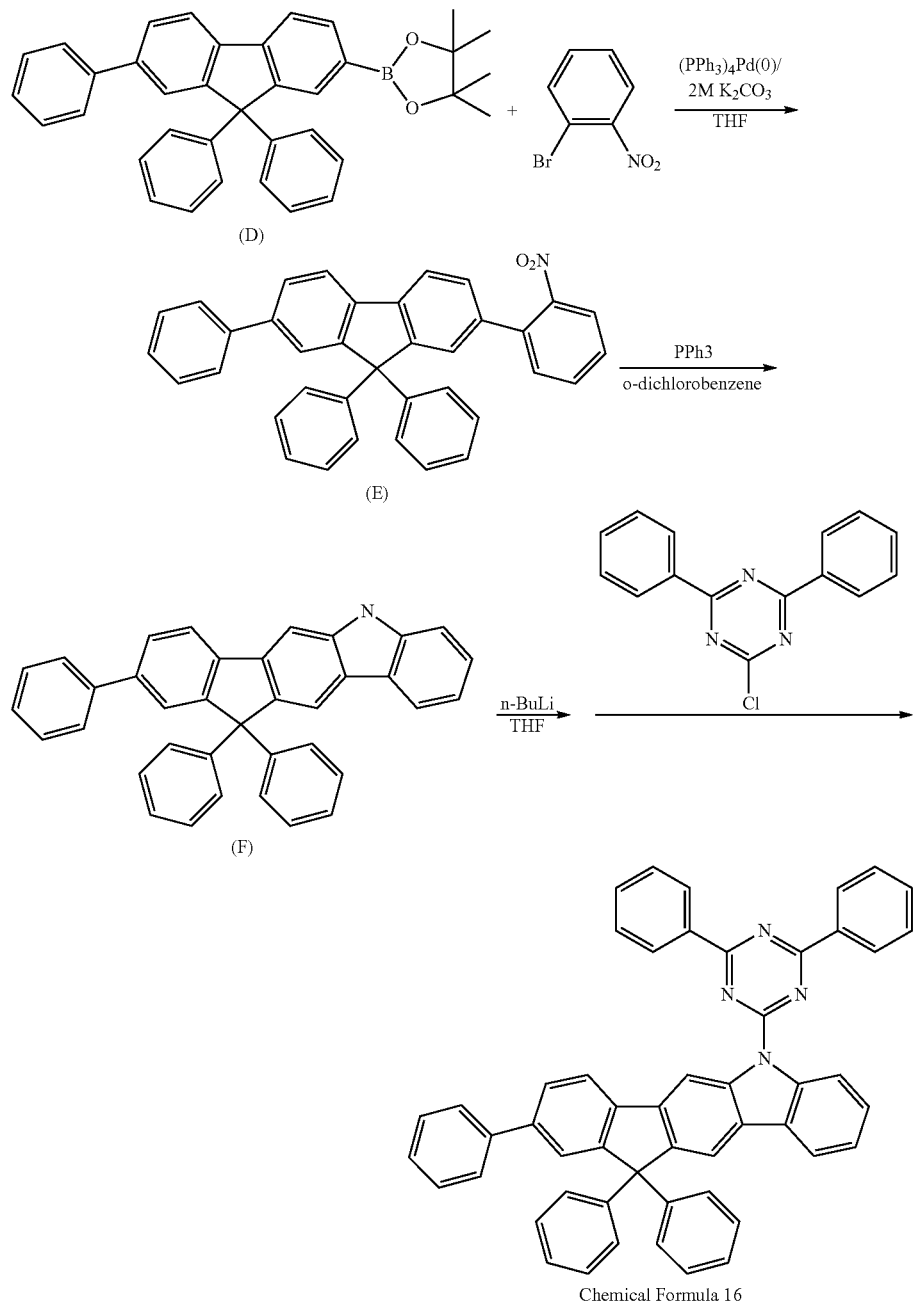

Chemical Formula 16

First Step: Synthesis of Intermediate Product (E)

10.0 g (19.2 mmol) of a compound D, 4.7 g (23.2 mmol) of 1-bromo-2-nitro benzene, and 0.8 g (0.69 mmol) of tetrakis (triphenylphosphine)palladium were dissolved in 200 mL of tetrahydrofuran in a 500 mL round-bottomed flask with a thermometer, a reflux-condenser, and an agitator under an argon atmosphere. 50 mL of tetratriethyl ammonium hydroxide with a concentration of 20% was added thereto. The mixture was agitated at 75° C. for 24 hours.

The resulting reactant was cooled down to room temperature to complete the reaction and then, extracted with methylene chloride and cleaned with water. Then, the reactant was treated with anhydrous magnesium sulfate and filtered to remove an organic solvent therein. The final residue was purified through silica gel chromatography using a mixed solvent prepared by mixing methylene chloride and hexane in a volume ratio of 1:1, obtaining 7 g of an intermediate product (E) (yield: 72%).

Second Step: Synthesis of Intermediate Product (F)

7 g (13.5 mmol) of the intermediate product (E) (synthesized in the first step) and 10.6 g (40.7 mmol) of triphenylphosphine were dissolved in 150 ml of dichlorobenzene. The mixture was heated and refluxed at 160° C. under an argon atmosphere.

The reactant was distilled to remove an organic solvent under reduced pressure and then, extracted with methylene chloride and cleaned with water. Next, the reactant was treated with anhydrous magnesium sulfate to remove moisture and filtered to remove an organic solvent therein. The final residue was purified through silica gel chromatography using a mixed solvent prepared by mixing methylene chloride and hexane in a volume ratio of 2:1, obtaining 4.3 g of an intermediate product (F) (yield: 65.9%).

Third Step: Synthesis of Compound for Organic Optoelectronic Device 4 g (8.27 mmol) of the intermediate product (F) (synthesized in the second step) was dissolved in 100 mL of anhydrous tetrahydrofuran (THF), and 6.2 mL of 1.6 M n-BuLi was slowly added thereto in a dropwise fashion at −78° C. The mixture was agitated for 30 minutes. Then, the mixture was further agitated at room temperature for 20 minutes, and 2.43 g (9.09 mmol) of 2-chloro-4,6-diphenyl triazine was added thereto at −78° C. The mixture was agitated at room temperature for 12 minutes.

The reactant was brought to room temperature to complete the reaction and then, extracted with methylene chloride and cleaned with water. Then, the reactant was treated with anhydrous magnesium sulfate to remove moisture and filtered to remove an organic solvent therefrom. The final residue was purified and recrystallized through silica gel chromatography using a mixed solvent prepared by mixing methylenechloride and hexane in a volume ratio of 1:3, obtaining 3.2 g of a compound (Chemical Formula 16) for an organic optoelectronic device (yield: 54.1%).

Atomic analysis was performed on the compound for an organic optoelectronic device. The results are provided as follows.

Calcd: C, 86.37; H, 4.79; N, 7.84
Found: C, 86.36; H, 4.80; N, 7.84

Preparation of Organic Light Emitting Diode

EXAMPLE 3

The compound synthesized according to Example 1 (as a host) and $Ir(PPy)_3$ (as a dopant) were used to fabricate an organic light emitting diode. Herein, an ITO layer was formed to be 1,000 Å thick to serve as an anode, while an aluminum (Al) layer was formed to be 1,500 Å thick to serve as a cathode.

In particular, an anode for an organic light emitting diode was fabricated by cutting an ITO glass substrate (with a sheet resistance of 15 $\Omega/cm^2$) to have a size of 50 mm×50 mm×0.7 mm and then, performing ultrasonic wave cleaning in acetone and isopropyl alcohol and pure water respectively for 15 minutes and UV ozone-cleaning for 30 minutes.

On the substrate, a 800 Å hole transport layer (HTL) was formed by depositing N,N'-di(1-naphthyl)-N,N-diphenyl-benzidine (NPB) (70 nm) and 4,4',4"-tri(N-carbazolyl)triphenylamine (TCTA) (10 nm) with a vacuum degree of 650× $10^{-7}$ Pa at a deposit speed ranging from 0.1 to 0.3 nm/s.

Then, a 300 Å-thick emission layer was formed by using the compound synthesized according to Example 1 under the same vacuum deposition conditions described above, and a phosphorescent dopant, $Ir(PPy)_3$, was simultaneously deposited. Herein, the phosphorescence dopant was deposited in an amount of 7 wt %, based on 100 wt % of a total weight of the emission layer, by regulating its deposition speed.

On the emission layer, a 50 Å-thick hole-blocking layer was formed by depositing aluminum(III) bis(2-methyl-8-quinolinato)-4-phenylphenolate (BAlq) under the same vacuum deposition conditions described above.

Then, a 200 Å-thick electron transport layer (ETL) was formed thereon by depositing $Alq_3$ under the same vacuum deposition conditions described above.

On the electron transport layer (ETL), LiF and Al were sequentially deposited to form a cathode, fabricating an organic light emitting diode.

The organic light emitting diode had a structure of ITO/NPB (70 nm)/TCTA (10 nm)/EML (the compound prepared in Example 1 (Chemical Formula 12) (93 wt %) of Example 1+$Ir(PPy)_3$ (7 wt %), 30 nm)/Balq (5 nm)/$Alq_3$ (20 nm)/LiF (0.5 nm)/Al (150 nm).

COMPARATIVE EXAMPLE 1

An organic light emitting diode was fabricated according to the same method as Example 3 except for using 4,4-N,N-dicarbazolebiphenyl (CBP) as a host for an emission layer instead of the compound of Example 1.

EXPERIMENTAL EXAMPLE 1

Performance Evaluation of Organic Light Emitting Diode

The organic light emitting diodes according to Example 3 and Comparative Example 1 were measured regarding current density change and luminance change depending on voltage and luminous efficiency. In particular, the current density change and luminance change depending on voltage and luminous efficiency were measured in the following method. The results are provided in Table 1, below.

(1) Current Density Change Depending on Voltage Change

Figure 6:
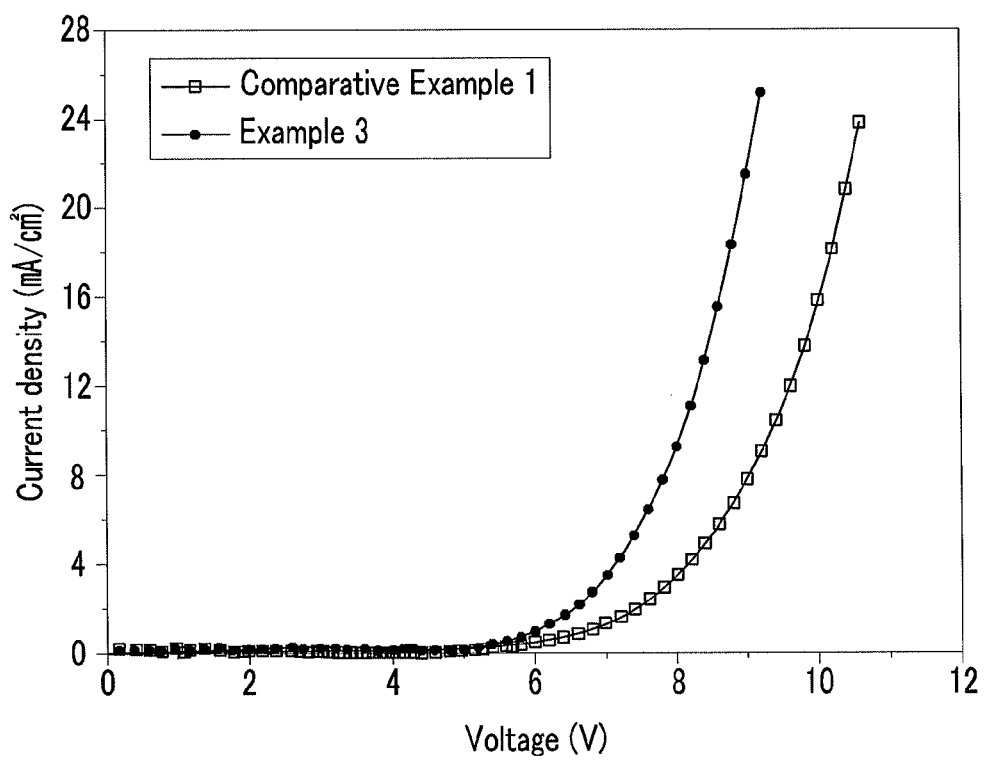
FIG. 6 illustrates a graph showing current density change depending on voltage of the organic light emitting diodes according to Example 3 and Comparative Example 1.

The organic light emitting diodes were measured regarding current using a current-voltage meter (Keithley 2400) while their voltages were increased from 0 V to 10 V. The results are provided in FIG. 6.

(2) Luminance Change Depending on Voltage Change

Figure 7:
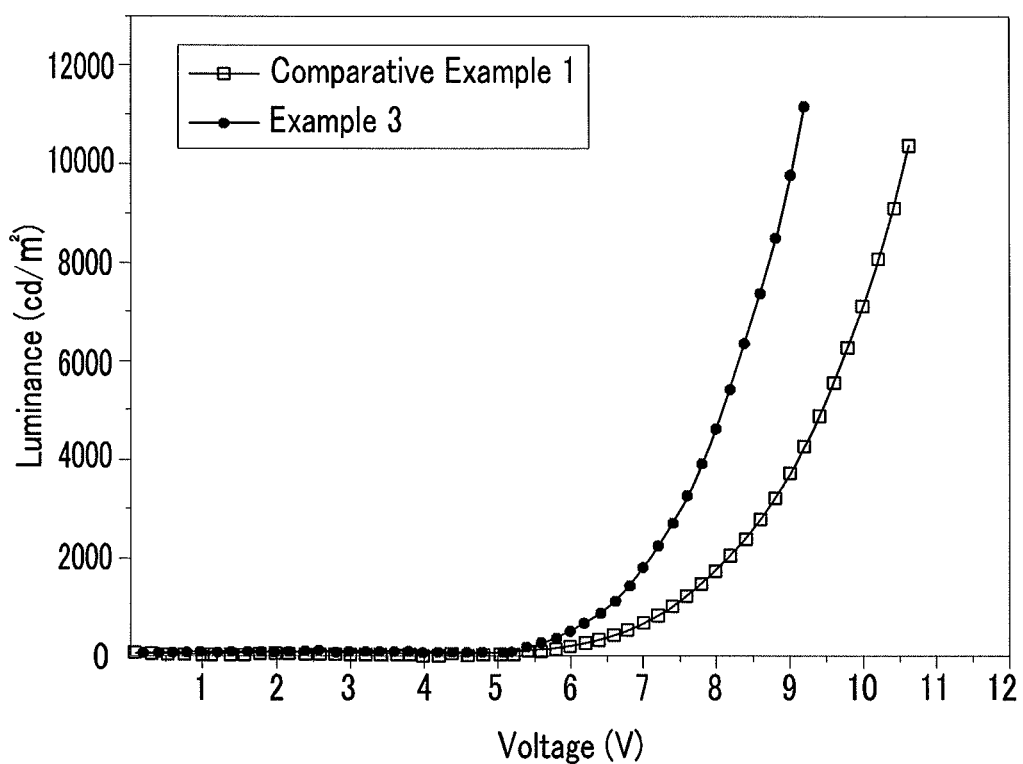
FIG. 7 illustrates a graph showing luminance change depending on voltage of the organic light emitting diodes according to Example 3 and Comparative Example 1.

The organic light emitting diodes were measured regarding luminance using a luminance meter (Minolta Cs-1000A), while their voltages were increased from 0 V to 10 V. The results are provided in FIG. 7.

(3) Luminous Efficiency

Figure 8:
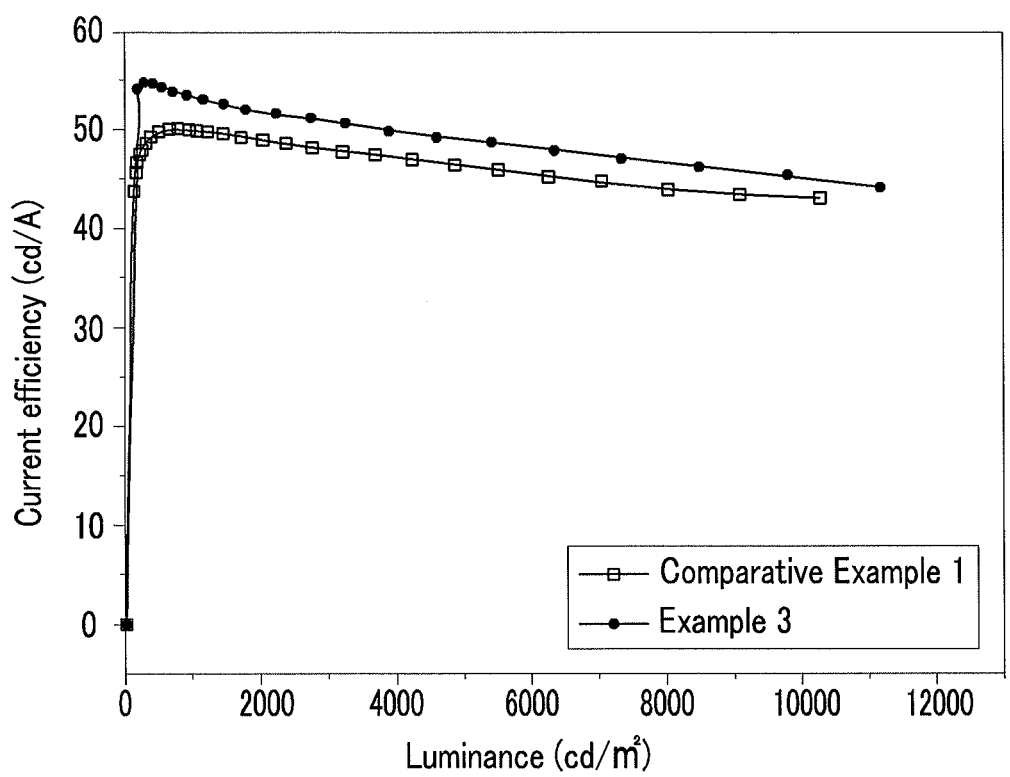
FIG. 8 illustrates a graph showing current efficiency change depending on luminance of the organic light emitting diodes according to Example 3 and Comparative Example 1.
Figure 9:
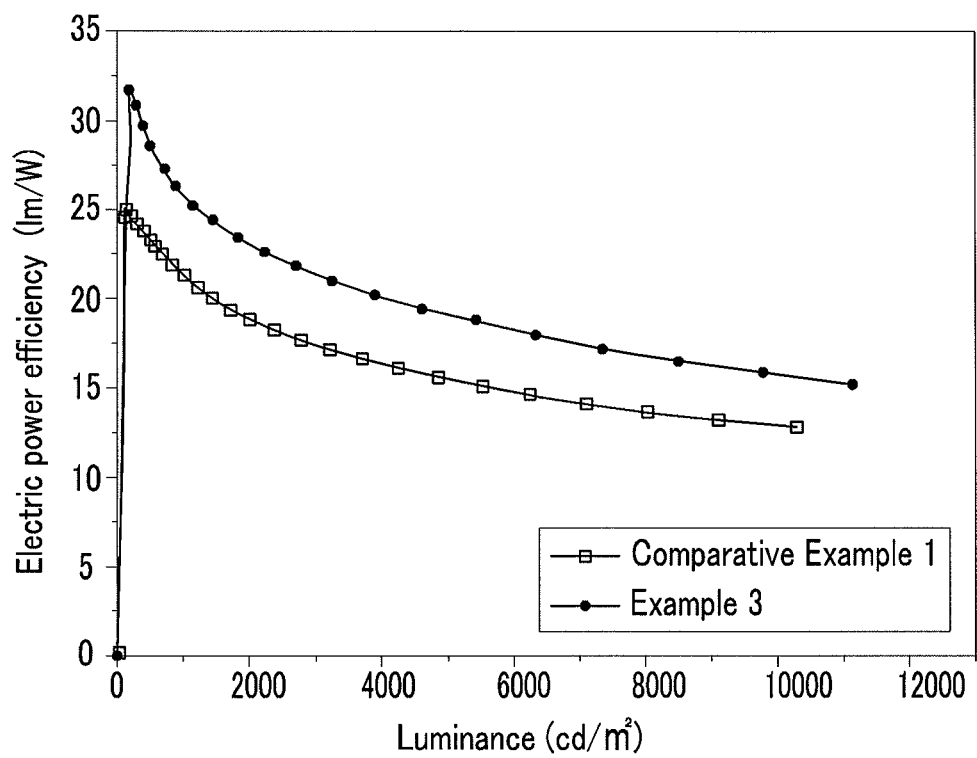
FIG. 9 illustrates a graph showing electric power efficiency change depending on luminance of the organic light emitting diodes according to Example 3 and Comparative Example 1.

The luminance and current density obtained in the above (1) and (2) and voltage were used to calculate current efficiency (cd/A) and electric power efficiency (lm/W) at the same luminance (2000 cd/m²). The results are provided in FIGS. 8 and 9.

(4) Color Coordinate

The organic light emitting diodes were measured regarding color coordinate using a luminance meter (Minolta Cs-100A). The results are provided in Table 1, below.

TABLE 1

| | | at 2000 cd/m² | | | |
|---|---|---|---|---|---|
| Device | Host material of emission layer | Driving voltage (V) | Current efficiency (cd/A) | Electric power efficiency (lm/W) | Color coordinate (x, y) |
| Example 3 | Example 1 | 7.2 | 51.8 | 22.6 | 0.308, 0.622 |
| Comparative Example 1 | CBP | 8.2 | 49.2 | 18.8 | 0.295, 0.622 |

Referring to Table 1, the organic light emitting diode of Example 3 had a driving voltage that was about 1 V lower than the driving voltage of the organic light emitting diode of Comparative Example 1. In addition, the organic light emitting diode of Example 3 had a much improved current efficiency and electric power efficiency, compared with the organic light emitting diode of Comparative Example 1. Accordingly, it may be seen that the compound according to Example 1 helped to lower driving voltage and to improve luminance and efficiency of an organic light emitting diode.

By way of summation and review, a dopant (along with a host material) may be included in an emission layer to increase efficiency and stability of organic light emitting diode. 4-N,N-dicarbazolebiphenyl (CBP) has been considered as a host material. However, CBP has high structural symmetry and may be easily crystallized. Due to low thermal stability, a short-circuit or a pixel defect may occur during heat resistance test of a device. Furthermore, host materials (such as CBP) may have faster hole transport speed than electron transport speed. Thus, an exciton may not be effectively formed in an emission layer, decreasing luminous efficiency of a device.

A low molecular weight host material may be deposited using a vacuum-deposition, which may cost more than a wet process. Further, low molecular weight host materials may have low solubility in an organic solvent. Thus, they may not be applied in a wet process and may not form an organic thin layer having excellent film characteristics.

Accordingly, in order to realize an organic photoelectric device with excellent efficiency and life-span, the embodiments provide a phosphorescent host material and a charge transport material having excellent electrical and thermal stability and bipolar characteristics (effectively transporting both holes and electrons) or a host material mixed with a material being capable of effectively transporting holes and electrons.

An embodiment provides a compound for an organic optoelectronic device having excellent thermal stability, and being capable of effectively transporting both holes and electrons.

Another embodiment provides an organic optoelectronic device including the compound for an organic optoelectronic device and having excellent efficiency and a driving voltage.

The compound for an organic optoelectronic device according to an embodiment may have excellent thermal stability, and particularly, may be applied to an organic thin layer of an organic optoelectronic device and thus may provide an organic optoelectronic device and a display device having high luminous efficiency at a low voltage and improved life-span.

Example embodiments have been disclosed herein, and although specific terms are employed, they are used and are to be interpreted in a generic and descriptive sense only and not for purpose of limitation. Accordingly, it will be understood by those of skill in the art that various changes in form and details may be made without departing from the spirit and scope of the present invention as set forth in the following claims.

[Chemical Formula 10]
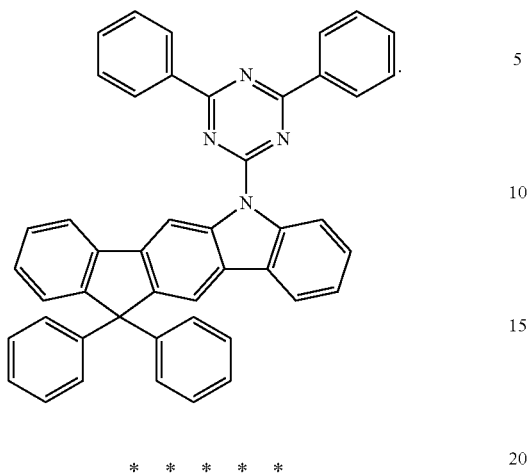

What is claimed is:

1. An organic light emitting diode, comprising:
an anode,
a cathode, and
at least one organic thin layer interposed between the anode and cathode,
wherein:
the at least one organic thin layer includes an emission layer that includes a host and a dopant, and
the host includes a compound for an organic optoelectronic device, the compound being represented by Chemical Formula 4:

[Chemical Formula 4]

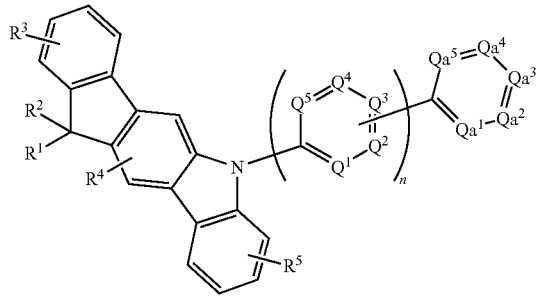

wherein, in Chemical Formula 4:
$Q^1$ to $Q^5$ and $Qa^1$ to $Qa^5$ are each independently N or CR, provided that one or more of $Qa^1$, $Qa^3$, and $Qa^5$ is N, and remaining ones of $Qa^1$, $Qa^3$, and $Qa^5$ are each independently CR, in which R is hydrogen, a substituted or unsubstituted C6 to C30 aryl group, a substituted or unsubstituted C3 to C30 heteroaryl group, or a combination thereof,
$R^1$, $R^2$, and $R^4$ are each independently hydrogen, a substituted or unsubstituted C6 to C30 aryl group, or a combination thereof,
$R^3$ and $R^5$ are each independently hydrogen or a substituted or unsubstituted C1 to C30 alkyl group, and
n is an integer of 0 to 5.

2. The organic light emitting diode as claimed in claim 1, wherein the compound for an organic optoelectronic device is represented by one of the following Chemical Formulae 10, 11, 12, 13, 14, or 15:

[Chemical Formula 10]

[Chemical Formula 11]

[Chemical Formula 12]

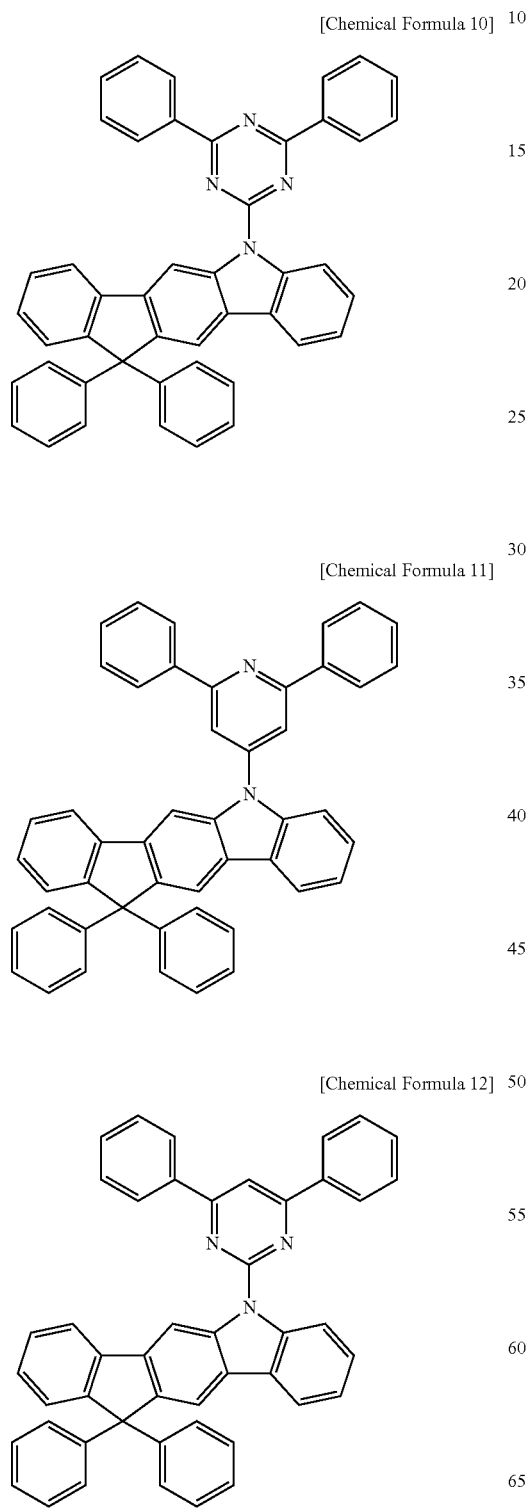

[Chemical Formula 13]

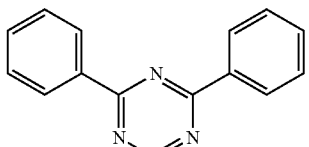

[Chemical Formula 14]

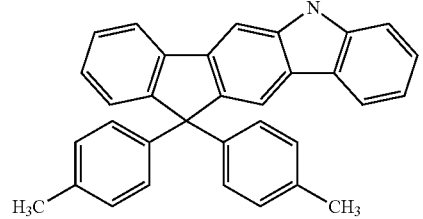

[Chemical Formula 15]

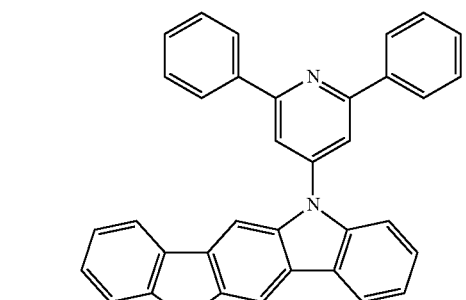

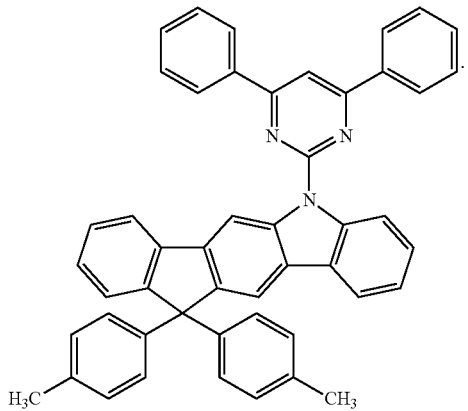

3. The organic light emitting diode as claimed in claim 1, wherein the compound for an organic optoelectronic device has a thermal decomposition temperature (Td) of about 350 to about 600° C.

4. A display device comprising the organic light emitting diode as claimed in claim 1.

5. The organic light emitting diode as claimed in claim 1, wherein:

the compound for an organic optoelectronic device is represented by the following Chemical Formula 10: